(12) United States Patent
Gidley-Baird et al.

(10) Patent No.: US 8,658,385 B2
(45) Date of Patent: *Feb. 25, 2014

(54) PURINERGIC (P2X) RECEPTORS IN EXTRA-CELLULAR BODY FLUID

(71) Applicants: Angus Gidley-Baird, North Ryde (AU); Julian Alexander Barden, North Ryde (AU)

(72) Inventors: Angus Gidley-Baird, North Ryde (AU); Julian Alexander Barden, North Ryde (AU)

(73) Assignee: Biosceptre International Limited (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/626,833

(22) Filed: Sep. 25, 2012

(65) Prior Publication Data

US 2013/0171666 A1    Jul. 4, 2013

Related U.S. Application Data

(63) Continuation of application No. 12/677,795, filed as application No. PCT/CT2008/001365 on Sep. 12, 2008, now Pat. No. 8,293,491.

(30) Foreign Application Priority Data

Sep. 14, 2007  (AU) ................ 2009705017

(51) Int. Cl.
  *G01N 33/53* (2006.01)
  *C07K 16/28* (2006.01)
(52) U.S. Cl.
  USPC ........... 435/7.23; 435/7.1; 435/7.2; 435/7.21; 530/387.1; 530/387.9; 530/388.22
(58) Field of Classification Search
  None
  See application file for complete search history.

(56) References Cited

U.S. PATENT DOCUMENTS

| | | | |
|---|---|---|---|
| 6,133,434 A | 10/2000 | Buell et al. | |
| 6,303,338 B1 | 10/2001 | Ni et al. | |
| 6,306,393 B1 | 10/2001 | Goldenberg et al. | |
| 6,329,503 B1 | 12/2001 | Afar et al. | |
| 6,709,832 B1 | 3/2004 | Von Knebel Doeberitz et al. | |
| 7,183,064 B1 | 2/2007 | Slater et al. | |
| 7,326,415 B2 | 2/2008 | Barden et al. | |
| 7,531,171 B2 | 5/2009 | Barden et al. | |
| 7,767,789 B2 | 8/2010 | Gorodeski et al. | |
| 7,888,473 B2 | 2/2011 | Barden et al. | |
| 8,067,550 B2 | 11/2011 | Barden et al. | |
| 8,080,635 B2 | 12/2011 | Barden et al. | |
| 8,293,491 B2 | 10/2012 | Gidley-Baird et al. | |
| 2004/0067542 A1 | 4/2004 | Barden et al. | |
| 2007/0020706 A1 | 1/2007 | Gorodeski et al. | |
| 2007/0248963 A1 | 10/2007 | Slater et al. | |
| 2008/0131438 A1 | 6/2008 | Barden et al. | |
| 2008/0227122 A1 | 9/2008 | Barden et al. | |
| 2009/0215727 A1 | 8/2009 | Douglas | |
| 2010/0036101 A1 | 2/2010 | Gidley-Baird et al. | |
| 2011/0110959 A1 | 5/2011 | Barden et al. | |
| 2011/0111431 A1 | 5/2011 | Slater et al. | |
| 2011/0177080 A1 | 7/2011 | Barden et al. | |
| 2012/0059151 A1 | 3/2012 | Barden et al. | |
| 2012/0282278 A1 | 11/2012 | Barden et al. | |

FOREIGN PATENT DOCUMENTS

| | | |
|---|---|---|
| AU | 64184/98 B2 | 10/1998 |
| CA | 2284859 C | 1/2007 |
| EP | 1006186 A1 | 10/1998 |
| WO | WO 92/16558 A1 | 10/1992 |
| WO | WO 95/33048 A2 | 12/1995 |
| WO | WO 97/06256 A2 | 2/1997 |
| WO | WO 97/41222 A1 | 11/1997 |
| WO | WO 98/42835 A1 | 10/1998 |
| WO | WO 00/50458 A1 | 8/2000 |
| WO | WO 01/06259 A1 | 1/2001 |
| WO | WO 01/30964 A2 | 5/2001 |
| WO | WO 02/48395 A1 | 6/2002 |
| WO | WO 02/057306 A1 | 7/2002 |
| WO | WO 03/020762 A1 | 3/2003 |
| WO | WO 2004/092384 A2 | 10/2004 |
| WO | WO 2007/027957 A2 | 3/2007 |
| WO | WO 2008/043145 A2 | 4/2008 |
| WO | WO 2008/043146 A1 | 4/2008 |
| WO | WO 2009/033233 A1 | 3/2009 |
| WO | WO 2009/033234 A1 | 3/2009 |
| WO | WO 01/00041 A1 | 1/2010 |
| WO | WO 2011/020155 A1 | 2/2011 |
| WO | WO 2011/075789 A1 | 6/2011 |
| WO | WO 2012/031333 A1 | 3/2012 |

OTHER PUBLICATIONS

U.S. Appl. No. 13/518,382, filed Jun. 21, 2012, Barden et al.
U.S. Appl. No. 60/686,770, filed Jun. 2, 2005, Gorodeski et al.
U.S. Appl. No. 60/778,993, filed Mar. 3, 2006, Gorodeski et al.
Ayyanathan et al., "Cloning and chromosomal localisation of the human P2Y1 purinoceptor," Biochem Biophys Res Commun, 218(3):783-788, (1996).
Barden et al., "Specific detection of non-functional human P2X7 receptos in HEK293 cells and B-lymphocytes," FEBS Letters, 538:159-162, (2003).
Bird et al., "Single-Chain Antigen-Binding Proteins," Science, 242(4877):423-426, (1988).
Bowler et al., "Identification and cloning of human P2U purinoceptor present in osteoclastoma, bone, and osteoblasts," J Bone Min Res, 10(7):1137-1145, (1995).
Buell et al., "P2X receptors: am emerging channel family," Eur J Neurosci., 8:2221-2228, (1996).
Buell et al.,"Blockade of Human P2X7 Receptor Function With a Monoclonal Antibody," Blood, 92:3521-3528, (1998).
Burnstock et al., "P2 Purinergic Receptors: Modulation of Cell Function and Therapeutic Potential," J Pharm Exp Therap, 295:862-869, (2000).

(Continued)

*Primary Examiner* — Christine J Saoud
*Assistant Examiner* — Jon M Lockard
(74) *Attorney, Agent, or Firm* — Alston & Bird LLP

(57) ABSTRACT

The invention relates to purinergic (P2X) receptors, to detection of protein in extra-cellular body fluids and to anti-bodies for the diagnosis or condition, especially cancer.

4 Claims, 19 Drawing Sheets

(56) References Cited

OTHER PUBLICATIONS

Chan et al., "Localization of P2X1 purinoceptors by autoradiography and immunohistochemistry in rat kidneys," Am J Physiol Renal Physiol, 274(4(2)): F799-804, (1998).

Cheewatrakoolpong et al., "Identification and characterization of splice variants of the human P2X7 ATP channel," Biochem Biophys Res Comm., 332:17-27, (2005).

Chessell et al., "Dynamics of P2X7 receptor pore dilation: pharmacological and functional consequences," Drug Dev Res, 53(2-3):60-65, (2001).

Communi et al., "Cloning and Functional Expression of a Human Uridine Nucleotide Receptor," J Biol Chem, 270(52): 30849-30852, (1995).

Communi et al., "Cloning, Functional Expression and Tissue Distribution of the Human P2Y6 Receptor," Biochem Biophys Res Commun, 222:303-308, (1996).

Dangl et al., "Rapid Isolation of Cloned Isotype Switch Variants Using Fluorescence Activated Cell Sorting," Cytometry, 2:395-401, (1982).

DeRisi et al., "Exploring the Metabolic and Genetic Control of Gene Expression on a Genomic Scale," Science, 278: 680-686, (1997).

Di Virgilio et al., "Responses of mouse lymphocytes to extracellular adenosine 5'triphosphaste (ATP)," J Immunol 143:1955-1960, (1989).

Di Virgiolio et al., "Purinergic P2X7 receptor: a pivotal role in inflammation and immunomodulation," Drug Dev Res, 45:207-213, (1998).

Dixon et al., "Extracellular nucleotides stimulate proliferation in MCF-7 breast cancer cells via P2-purinoceptors," Br J Cancer, 75(1):34-39, (1997).

Dubyak et al., "Signal transduction via P2-purinergic receptors for extracellular ATP and other nucleotides," Am. J Physiol 265:C577-C606,(1993).

European Search Report of Sep. 18, 2008 for application EP08156593 (published as EP1961767).

Feng et al., "A truncated P2X7 receptor variant (P2X7-j) endogenously expressed in cervical cancer cells antagonizes the full-length P2X7 receptor through hetero-oligomerization," J Biol Chem, 281:17228-17237, (2006).

Feng et al., "ATP stimulates GRK-3 phosphorylation and 3-arrestin-2-dependent internalization of P2X7 receptor," Am J Physiol Cell Physiol, 288:C1342-C1356, (2005).

Feng et al., "Endogenously Expressed Truncated P2X, Receptor Lacking the C-Terminal (P2X7-RTr) is Preferentially Upregulated in Epithelial Cancer Cells and Fails to Mediate Ligand-Induced Pore Formation and Apoptosis," 10th Symposium European Society for (2006).

Feng et al., "Endogenously Expressed Truncated P2X7 Receptor Lacking the C-Terminus is Preferentially Upregulated in Epithelial Cancer Cells and Fails to Mediate Ligand-Induced Pore Formation and Apoptosis," Nucleosides and Nucleic Acids, 25:1271-(2006).

Ferrari et al., "P2Z purinoreceptor ligation induces activation of caspases with distinct roles in apoptotic and necrotic alterations of cell death," FEBS Lett., 447:71-75, (1999).

Ferrari et al., "ATP-mediated cytoxicity in microglial cells," Neuropharmacology, 36 (9):1295-1301, (1997).

Foster et al., "Cellular and molecular pathology of prostate cancer precursors," Scand J Urol Nephrol Suppl.,34(205):19-43, (2000).

Galfre et al., "Antibodies to major histocompatability antigens produced by hybrid cell lines," Nature, 266:550-552, (1977).

Galfre et al., "Rat x rat hybrid myelomas and a monoclonal anti-Fd portion of mouse IgG," Nature, 277:131-133, (1979).

Getter et al., "A simple method for polyethylene glycol-promoted hybridization of mouse myeloma cells," Somatic Cell Genet., 3(2):231, (1977).

GenBank: Accession No. Y09561, versions Y09561.1, "*H. sapiens* mRNA for P2X7 receptor". [Retrieved from the Internet May 24, 2011: <URL: http://www.ncbi.nlm.nih.gov/nuccore/y09561 >].

Georgiou et al., "Human Epidermal and Monocyte-Derived Langerhans Cells Express Functional P2X7 Receptors," J Invest Dermatology,125:482-490, (2005).

Giusti et al., "Somatic diversification of S107 from an antiphosphocholine to an anti-DNA autoantibody is due to a single base change in its heavy chain variable region," PNAS, 84:2926-2930, (1987).

Greenbaum et al., "Comparing protein abundance and mRNA expression levels on a genomic scale," Genome Biology, 4(9):117.1-117.8, (2003).

Greig et al., "Expression of Purinergic Receptors in Non-melanoma Skin Cancers and Their Functional Roles in A431 Cells," J Invest Dermatol, 121:315-327, (2003).

Groschel-Stewart et al., "Localisation of P2X5 and P2X7 receptors by immunohistochemistry in rat stratified squamous epithelia," Cell Tissue Res, 296:599-605, (1999).

Gu et al, "A Glu-496 to Ala Polymorphism leads to loss of function of the human P2X7 receptor," J Biol Chem, 276(14):11135-11142, (2001).

Gu et al., "An Arg307 to Gln Polymorphism within the ATP-binding Site Causes Loss of Function of the Human P2X7 Receptor," J Biol Chem, 279 (30):31287-31295, (2004).

Gussow et al., "Humanization of Monoclonal Antibodies," Methods in Enzymology, 203:99-121, (1991).

Hansen et al., "Structural Motif and Characteristics of the Extracellular Domain of P2X Receptors," Biochem and Biophys Res Comm, 236(3):670-675, (1997).

Hansen et al., "The distribution of single P (2 ×1)—receptor clusters on smooth muscle cells in relation to nerve varicosities in the ret urinary bladder," J Neurocytol, 27(7): 529-539, (1998).

Holliger et al., "'Diabodies': Small bivalent and bispecific antibody fragments," Proc. Natl. Acad Sci. USA, 90:6444-6448, (1993).

Hopfner et al, "Expression of functional P2-purinergic receptors in primary cultures of human colorectal carcinoma cells," Biochem and Biophys Res Comm, 251:811-817, (1998).

Humphrey, "Gleason grading and prognostic factors in carcinoma of the prostate," Modern Pathology, 17:292-306, (2004).

Huston et al., "Protein engineering of antibody binding sites: Recovery of specific activity in an anti-digoxin single-chain Fv analogue produced in *Escherichia coli*," Proc. Natl. Acad. Sci. USA, 85:5879-5883, (1988).

Jacob et al., "Cytogenetic Profile of Chronic Myeloid Leukemias," Indian J Cancer, 39(2):61-65, (2002).

Jameison et al., "Extracellular ATP causes loss of L-selectin from human lymphocytes via occupancy of P2Z purinoceptors," J Cell Physiol, 166:637-642 (1996).

Janssens et al., "Effects of extracellular nucleotides and nucleosides on prostate carcinoma cells," Br J Pharmacol., 132: 536-46, (2001).

Jantzen et al., "Evidence for Two Distinct G-protein-coupled ADP Receptors Mediating Platelet ctivation," Thromb and Haemost, 81:111-117, (1999).

Jones, "Critically assessing the state-of-the-art in protein structure prediction,"Pharmacogenomics Journal, 1:126-134, (2001).

Katzur et al., "Expression and responsiveness of P2Y2 receptors in human endometrial cancer cell lines," J Clin Endocrinol Metab., 84(11): 4085-4091, (1999).

Kennedy et al., "The discovery and development of P2 receptor subtypes," J Auto Nerv Syst, 81:158-163, (2000).

Kim et al., "Differential Assembly of Rat Purinergic P2X7 Receptor in Immune Cells of the Brain and Periphery," J Biol Chem, 276(26):23262-23267, (2001).

King et al., "Metabotropic receptors for ATP and UTP: exploring the correspondence between native and recombinant nucleotide receptors," TiPS, 19: 506-514, (1998).

Kishore et al., "Cellular localisation of P2Y2 purinoceptor in rat renal inner medulla and lung," Am J Physiol Renal Physiol, 278: F43-F51, (2000).

La Sala et al., "Alerting and tuning the immune response by extracellular Nucleotides," J Leukoc Biol, 73:339-343, (2003).

Lee et al., "P2X receptor immunoreactivity in the male genital organs of the rat," Cell Tissue Res, 300(2): 321-330, (2000).

(56) References Cited

OTHER PUBLICATIONS

Li et al., "P2X7 Receptor: A Novel Biomarker of Uterine Epithelial Cancers," Cancer Epidemiol Biomarkers Prev, 15(10):1906-1913, (2006).
Mager et al., "Prediction of the confirmation of the human P2X7 receptor," Letts Drug Des Discov, 410):675-682, (2006).
Maier et al., "Cloning of P2Y6 cDNAs and Identification of a Pseudogene: Comparison of P2Y Receptor Subtype Expression in Bone and Brain Tissues," Biochem and Biophys Res Comm, 237:297-302, (1997).
Mariuzza et al., "The structural basis of antigen-antibody recognition," Annual Review of Biophysics and Biophysical Chemistry, 16:139-159, (1987).
Mauro et al., "Chronic myelogenous leukaemia," Curr Opin Oncol, 13(1):3-7, (2001).
Meeker et al., "An additional breakpoint region in the BCL-1 locus associated with the t(11;14)(q13;q32) translocation of B-lymphocytic malignancy," Blood, 74:1801-1806, (1989).
Nawa et al., "Frequent loss of expression or aberrant alternative splicing of P2XM, a p53-inducible gene, in soft-tissue tumours," Br J Cancer, 80(8):1185-89, (1999).
Ngo et al "Computational complexity, protein structure prediction, and the Levinthal paradox," In Merz and Le Grand (eds), The protein folding problem and tertiary structure prediction, Birkhauser: Boston, pp. 491-495, (1994).
Nihei et al., "Pharmacologic properties of P2z/P2X7 receptor characterized in murine dendritic cells: role on the induction of apoptosis", Blood, 96(3)996-1005, (2000).
Parr et al., "Cloning and expression of a human P2U nucleotide receptor, a target for cystic fibrosis pharmacotherapy," Proc. Natl. Acad. Sci. USA, 91:3275-3279, (1994).
Paul, Fundamental Immunology, Lippincott Williams & Wilkins, p. 107, (1998).
PCT International Preliminary Examination Report of Mar. 14, 2003 for application PCT/AU2001/001614.
PCT International Preliminary Examination Report of May 1, 2003 for application PCT/AU02/00061.
PCT International Preliminary Examination Report of Aug. 1, 2001 for application PCT/AU00/00363.
PCT International Preliminary Examination Report of Dec. 17, 2003 for application PCT/AU02/001204.
PCT International Preliminary Report on Patentability of Jan. 5, 2011 for application PCT/AU09/000869.
PCT International Preliminary Report on Patentability of Mar. 16, 2010 for application PCT/AU08/001364.
PCT International Preliminary Report on Patentability of Mar. 16, 2010 for application PCT/AU08/001365.
PCT International Preliminary Report on Patentability of Apr. 15, 2009 for application PCT/AU07/001540.
PCT International Preliminary Report on Patentability of Apr. 15, 2009 for application PCT/AU07/001541.
PCT International Preliminary Report on Patentability of Jun. 26, 2012 for application PCT/AU2010/001741.
PCT International Search Report for application PCT/AU2010/001741 mailed Feb. 11, 2011.
PCT International Search Report of Feb. 5, 2002 for application PCT/AU2001/001614.
PCT International Search Report of Apr. 2, 2002 for application PCT/AU02/00061.
PCT International Search Report of Jul. 21, 2000 for application PCT/AU00/00363.
PCT International Search Report of Aug. 7, 2009 for application PCT/AU09/000869.
PCT International Search Report of Sep. 22, 2010 for application PCT/AU10/001070.
PCT International Search Report of Oct. 14, 2002 for application PCT/AU02/001204.
PCT International Search Report of Oct. 27, 2008 for application PCT/AU08/001364.
PCT International Search Report of Nov. 9, 2007 for application PCT/AU07/001541.
PCT International Search Report of Nov. 21, 2008 for application PCT/AU08/001365.
PCT International Search Report of Nov. 2007 for application PCT/AU07/001540.
Peng et al., "P2Z purinoceptor, a special receptor for apoptosis induced by ATP in human leukemic lymphocytes," Chinese Med J, 112(4):356-362, (1999).
Perou et al., "Distinctive gene expression patterns in human mammary epithelial cells and breast cancers," Proc. Natl. Acad. Sci. USA, 96:9212-9217, (1999).
Poljak et al., "Production and structure of diabodies," Structure, 2:1121-1123, (1994).
Ralevic et al., "Receptors for Purines and Pyrimidines," Pharmacol Rev., 50(3):413-492, (1998).
Rassendren et al., "The permeabilizing ATP receptor, P2X7: Cloning and expression of a human cDNA," J Biol Chem, 272(9):5482-5486, (1997).
Ray et al., "Purinergic receptor distribution in endothelial cells in blood vessels: a basis for selection of coronary artery grafts," Atherosclerosis, 162:55-61, (2002).
Romagnoli et al., "Recent progress in the discovery of antagonists acting at P2X7 receptor," Expert Opinions Ther. Patents, 15(3):271-287, (2005).
Rudikoff et al., "Single amino acid substitution altering antigen-binding specificity," PNAS, 79:1979-1983, (1982).
Sauer et al., "Calcium-dependence of hydrogen peroxide-induced c-fos expression and growth stimulation of multicellular prostate tumour spheroids," FEBS Lett, 419: 201-205, (1997).
Schultze-Mosgau et al., "Characterization of calcium-mobilizing, purinergic P2Y2 receptors in human ovarian cancer cells," Mol Human Reproduct., 6(5): 435-442, (2000).
Slater et al. "Early prostate cancer detected using expression of non-functional cytolytic P2X7 receptors," Histopathology, 44:206-215, (2004).
Slater et al., "Detection of preneoplasia in histologically normal prostate biopsies," Prost Cancer Prostat Dis, 4:92-96, (2001).
Slater et al., "Differentiation between cancerous and normal hyperplastic lobules in breast lesions," Breast Cancer Res Treat, 83:1-10, (2004).
Slater et al., "Expression of the apoptotic calcium channel P2X7 in the glandular epithelium is a marker for early prostate cancer and correlates with increasing PSA levels," J Mol Histol., 36:159-165, (2005).
Slater et al., "Increased expression of apoptotic markers in melanoma," Melanoma Res, 13(2):137-145, (2003).
Slater et al., "Markers for the development of early prostate cancer," J Pathol,199:368-377, (2003).
Sluyter et al., "Extracellular ATP increases cation fluxes in human erthrocytes by activation of the P2X7 receptor," J Biol Chem, 279(43):44749-44756, (2004).
Spieker-Polet et al., "Rabbit monoclonal antibodies: Generating a fusion partner to produce rabbit-rabbit hybridomas," Proc. Natl. Acad. Sci USA, 92:9348-9352, (1995).
Supplementary European Search Report and European Search Opinion for application EP08800000 (published as EP2201026) mailed Oct. 29, 2012.
Supplementary European Search Report and European Search Opinion for application EP09771858 (published as EP2318438) mailed Oct. 24, 2012.
Supplementary European Search Report of Mar. 4, 2011 for application EP01270623 (published as EP1352085).
Supplementary European Search Report of May 21, 2010 for application EP07815345 (published as EP2082032).
Supplementary European Search Report of Aug. 16, 2010 for application EP08800001 (published as EP2201377).
Supplementary European Search Report of Nov. 8, 2002 for application EP00918600 (published as EP1179183).
Supplementary Partial European Search Report of Apr. 29, 2005 for application EP02715313 (published as EP1360203).
Surprenant et al., "The cytosolic P2Z receptor for extracellular ATP identified as a P2X receptor (P2X7)," Science, 272:735-738, (1996).

(56) References Cited

OTHER PUBLICATIONS

Tockman et al., "Considerations in Bringing a Cancer Biomarker to Clinical Application," Cancer Res, 52:2711s-2718s, (1992).
Torres et al., "Hetero-oligomeric Assembly of P2X Receptor Subunits," J Biol Chem, 274(10):6653-6659, (1999).
Tosatto et al., "Large-Scale Prediction of Protein Structure and Function from Sequence," Current Pharmaceutical Design, 12:2067-2086, (2006).
U.S. Appl. No. 10/019,356 (now Patent No. 7,183,064), Final Office Action mailed May 9, 2006.
U.S. Appl. No. 10/019,356 (now Patent No. 7,183,064), Non-Final Office Action mailed Jul. 19, 2005.
U.S. Appl. No. 10/019,356 (now Patent No. 7,183,064), Notice of Allowance mailed Oct. 11, 2006.
U.S. Appl. No. 10/019,356 (now Patent No. 7,183,064), Requirement for Restriction/Election mailed Mar. 18, 2005.
U.S. Appl. No. 10/450,205 (now Abandoned, Publication No. 2004/0067542), Final Office Action mailed Sep. 7, 2007.
U.S. Appl. No. 10/450,205 (now Abandoned, Publication No. 2004/0067542), Non-Final Office Action mailed Dec. 19, 2006.
U.S. Appl. No. 10/450,205 (now Abandoned, Publication No. 2004/0067542), Requirement for Restriction/Election mailed Sep. 6, 2006.
U.S. Appl. No. 10/622,313 (now Patent No. 7,326,415), Non-Final Office Action mailed Nov. 30, 2006.
U.S. Appl. No. 10/622,313 (now Patent No. 7,326,415), Notice of Allowance and Examiner Interview Summary Record mailed Sep. 5, 2007.
U.S. Appl. No. 10/622,313 (now Patent No. 7,326,415), Requirement for Restriction/Election mailed Jun. 16, 2006.
U.S. Appl. No. 11/566,472 (now Abandoned, Publication No. 2007/0248963), Examiner Interview Summary Record mailed Dec. 30, 2009.
U.S. Appl. No. 11/566,472 (now Abandoned, Publication No. 2007/0248963), Final Office Action mailed Jan. 12, 2009.
U.S. Appl. No. 11/566,472 (now Abandoned, Publication No. 2007/0248963), Final Office Action mailed Mar. 9, 2010.
U.S. Appl. No. 11/566,472 (now Abandoned, Publication No. 2007/0248963), Non-Final Office Action mailed Jun. 16, 2008.
U.S. Appl. No. 11/566,472 (now Abandoned, Publication No. 2007/0248963), Non-Final Office Action mailed Aug. 26, 2009.
U.S. Appl. No. 11/566,472 (now Abandoned, Publication No. 2007/0248963), Requirement for Restriction/Election mailed Dec. 17, 2007.
U.S. Appl. No. 11/968,607 (now Patent No. 7,531,171), Non-Final Office Action mailed Sep. 26, 2008.
U.S. Appl. No. 11/968,607 (now Patent No. 7,531,171), Notice of Allowance mailed Jan. 9, 2009.
U.S. Appl. No. 11/968,607 (now Patent No. 7,531,171), Requirement for Restriction/Election mailed Aug. 19, 2008.
U.S. Appl. No. 12/043,083 (now Abandoned, Publication No. 2008/0227122), Non-Final Office Action mailed Nov. 26, 2010.
U.S. Appl. No. 12/043,083 (now Abandoned, Publication No. 2008/0227122), Notice of Allowance mailed Aug. 5, 2011.
U.S. Appl. No. 12/043,083 (now Abandoned, Publication No. 2008/0227122), Requirement for Restriction/Election mailed Jul. 21, 2010.
U.S. Appl. No. 12/417,989 (now Patent No. 7,888,473), Non-Final Office Action mailed Jun. 16, 2010.
U.S. Appl. No. 12/417,989 (now Patent No. 7,888,473), Notice of Allowance mailed Sep. 24, 2010.
U.S. Appl. No. 12/445,258 (now Abandoned, Publication No. 2010/0036101), Non-Final Office Action mailed Oct. 18, 2011.
U.S. Appl. No. 12/445,258 (now Abandoned, Publication No. 2010/0036101), Requirement for Restriction/Election mailed May 6, 2011.
U.S. Appl. No. 12/445,273 (now Patent No. 8,067,550), Non-Final Office Action mailed Oct. 1, 2010.
U.S. Appl. No. 12/445,273 (now Patent No. 8,067,550), Notice of Allowance mailed Mar. 30, 2011.
U.S. Appl. No. 12/445,273 (now Patent No. 8,067,550), Notice of Allowance mailed Jul. 8, 2011.
U.S. Appl. No. 12/445,273 (now Patent No. 8,067,550), Requirement for Restriction/Election mailed Aug. 9, 2010.
U.S. Appl. No. 12/677,795 (now Patent No. 8,293,491), Notice of Allowance mailed Jun. 22, 2012.
U.S. Appl. No. 12/677,795 (now Patent No. 8,293,491), Restriction/Election Requirement mailed Oct. 12, 2011.
U.S. Appl. No. 12/677,799, Non-Final Office Action mailed Jun. 21, 2012.
U.S. Appl. No. 12/677,799, Notice of Allowance and Examiner Interview Summary Record mailed Dec. 10, 2012.
U.S. Appl. No. 12/677,799, Requirement for Restriction/Election mailed Feb. 23, 2012.
U.S. Appl. No. 12/878,865 (now Abandoned, Publication No. 2011/0111431), Non-Final Office Action mailed Oct. 20, 2011.
U.S. Appl. No. 12/878,865 (now Abandoned, Publication No. 2011/0111431), Requirement for Restriction/Election mailed Mar. 25, 2011.
U.S. Appl. No. 12/975,341 (now Patent No. 8,080,635), Non-Final Office Action mailed Mar. 24, 2011.
U.S. Appl. No. 12/975,341 (now Patent No. 8,080,635), Notice of Allowance mailed Aug. 17, 2011.
U.S. Appl. No. 13/002,647, Requirement for Restriction/Election mailed Aug. 7, 2012.
U.S. Appl. No. 13/298,222, Final Office Action mailed Sep. 7, 2012.
U.S. Appl. No. 13/298,222, Non-Final Office Action mailed Feb. 13, 2012.
U.S. Appl. No. 13/298,222, Notice of Allowance and Examiner Interview Summary Record mailed Nov. 27, 2012.
U.S. Appl. No. 12/677,795 (now Patent No. 8,293,491), Non-Final Office Action mailed Feb. 29, 2012.
Uniprot entry Q4VKI0_Human P2X7 Isoform E, UniProt Consortium, (2005).
Uniprot entry Q4VKI1_Human P2X7 Isoform F, UniProt Consortium, (2005)
Urano et al., "Cloning of P2XM, a novel human P2X receptor gene regulated by p53," Cancer Res, 57:3281-87, (1997).
Virginio et al., "Kinetics of cell lysis, dye uptake and permeability changes in cells expressing the rat P2X7 receptor," J Physiol., 519(2):335-346, (1999).
von Kugelgen et al., "Molecular Pharmacology of P2Y-receptors," Naunyn Scmiedebergs Arch Pharmacol, 362:(4-5)310-323 (2000).
Vulchanova et al., "Immunohistochemical study of the P2X2 and P2X3 receptor subunits in rat and monkey sensory neurons and their central terminals," Neuropharmacol, 36(9):1229-1242, (1997).
Wagstaff et al., "Extracellular ATP activates multiple signalling pathways and potentiates growth factor-induced c-fos gene expression in MCF-7 breast cancer cells," Carcinogenesis 21(12):2175-2181, (2000).
Wang et al., "P2X7 receptor-mediated apoptosis of human cervical epithelial cells," Am. J Physiol, 287:1349-1358, (2004).
Ward et al., "Binding activities of a repertoire of single immunoglobulin variable domains secreted from *Escherichia coli*," Nature 341:544-546, (1989).
Wasilenko et al., "Calcium signaling in prostate cancer cells: Evidence for multiple receptors and enhanced sensitivity to bombesin/GRP," The Prostate 30:167-173 (1997).
Wells "Additivity of mutational effects in proteins," Biochemistry, 29(37):8509-8517, (1990).
White et al., "P2Y purinergic receptors regulate the growth of human melanomas," Cancer Letts, 224:81-91, (2005).
Wiley et al., "A single nucleotide polymorphism is associated with loss of function of the monocyte P2X7 receptor," Blood, 96(11)1 7 (2000). Abstract.
Wiley et al., "An Ile-568 to Asn polymorphism prevents normal trafficking and function of the human P2X7 receptor," J Biol Chem 278 (19):17108-17113, (2003).
Wiley et al., "Genetic polymorphisms of the human P2X7 receptor and relationship to function," Drug Dev Res, 53(2-3):72-76, (2001).
Williams et al., "Purinergic and pyrimidinergic receptors as potential drug targets," Biochem Pharm, 59:1173-1184, (2000).

(56) References Cited

OTHER PUBLICATIONS

Winkler et al., "Changing the antibody binding specificity by single point mutations of an Anti-p24 (HIV-1) antibody," Journal of Immunology, 165:4505-4514, (2000).

Worthington et al., "Point mutations confer loss of ATP-induced human P2X7 receptor function," FEBS Lett, 512:43-46, (2002).

Wurl et al., "High prognostic significance of Mdm2/p53 co-overexpression in soft tissue sarcomas of the extremities," Oncogene,16(9):1183-85, (1998).

Casset et al., "A peptide mimetic of an anti-CD4 monoclonal antibody by rational design," Biochemical and Biophysical Research Communications, 307:198-205, (2003).

Colman, "Effects of amino acid sequence changes on antibody-antigen interactions," Research in Immunology, A Structural View of Immune Recognition by Antibodies, 55th Forum in Immunology, 145:33-36, (1994).

Gu et al., "Expression of P2X7 purinoceptors on human lymphocytes and monocytes: evidence for nonfunctional P2X 7 receptors," Am J Physiol Cell Physiol, 279:C1189-C1197, (2000).

MacCallum et al, "Antibody-antigen Interactions: Contact Analysis and Binding Site Topography," J. Mol. Biol., 262:732-745, (1996).

Paul, Fundamental Immunology, 3rd Edition, Raven Press, New York, Chapt. 9, pp. 292-295 (1993).

PCT International Preliminary Report on Patentability of Mar. 12, 2013 for application PCT/AU2011/001166.

PCT International Search Report of Nov. 4, 2011 for application PCT/AU2011/001166.

Roman et al., "Cloning and Pharmacological Characterization of the Dog P2X7 Receptor," British Journal of Pharmacology, 158:1513-1526, (2009).

Supplementary European Search Report and European Search Opinion for application EP10838429 (published as EP2516470) mailed Apr. 13, 2013.

U.S. Appl. No. 12/677,799, Notice of Allowance mailed Jan. 9, 2013.

U.S. Appl. No. 13/002,647, Non-Final Office Action mailed Dec. 20, 2012.

U.S. Appl. No. 13/002,647, Notice of Allowance mailed Aug. 2, 2013.

U.S. Appl. No. 13/518,382, Non-Final Office Action mailed Jun. 18, 2013.

U.S. Appl. No. 13/518,382, Requirement for Restriction/Election mailed Mar. 21, 2013.

U.S. Appl. No. 13/766,630, Non-Final Office Action mailed Aug. 19, 2013.

U.S. Appl. No. 13/518,382, Non-Final Office Action mailed Sep. 18, 2013.

Uniprot sequence entry: Accession No. Q4VKH8, "P2X7 isoform H," Jul. 2005. [Retrieved from the Internet Sep. 9 2013: <URL: http:// www.ncbi.nlm.nih.gov/protein/Q4VKH8>].

Uniprot sequence entry: Accession No. Q4VKH9, "P2X7 isoform G," Jul. 2005. [Retrieved from the Internet Sep. 9, 2013: <URL: http:// www.ncbi.nlm.nih.gov/protein/Q4VKH9>].

Uniprot sequence entry: Accession No. Q4VKI2, "P2X7 isoform D," Jul. 2005. [Retrieved from the Internet Sep. 9, 2013: <URL: http:// www.ncbi.nlm.nih.gov/protein/Q4VKI2>]

Uniprot sequence entry: Accession No. Q4VKI4, "P2X7 isoform B," Jul. 2005. [Retrieved from the Internet Sep. 9, 2013: <URL: http:// www.ncbi.nlm.mh.gov/protein/Q4VKI4>].

Figure 1

HUMAN P2X₇

| | | | | | |
|---|---|---|---|---|---|
| 1 | MPACCSCSDV | FQYETNKVTR | IQSMNYGTIK | WFFHVIIFSY | VCFALVSDKL | YQRKEPVISS |
| 61 | VHTKVKGIAE | VKEEIVENGV | KKLVHSVFDT | ADYTFPLQGN | SFFVMTNFLK | TEGQEQRLCP |
| 121 | EYPTRRTLCS | SDRGCKKGWM | DPQSKGIQTG | RCVVHEGNQK | TCEVSAWCPI | EAVEEAPRPA |
| 181 | LLNSAENFTV | LIKNNIDFPG | HNYTTRNILP | GLNITCTFHK | TQNPQCPIFR | LGDIFRETGD |
| 241 | NFSDVAIQGG | IMGIEIYWDC | NLDRWFHHCR | PKYSFRRLDD | KTTNVSLYPG | YNFRYAKYYK |
| 301 | ENNVEKRTLI | KVFGIRFDIL | VFGTGGKFDI | IQLVVYIGST | LSYFGLAAVF | IDFLIDTYSS |
| 361 | NCCRSHIYPW | CKCCQPCVVN | EYYYRKKCES | IVEPKPTLKY | VSFVDESHIR | MVNQQLLGRS |
| 421 | LQDVKGQEVP | RPAMDFTDLS | RLPLALHDTP | PIPGQPEEIQ | LLRKEATPRS | RDSPVWCQCG |
| 481 | SCLPSQLPES | HRCLEELCCR | KKPGACITTS | ELFRKLVLSR | HVLQFLLLYQ | EPLLALDVDS |
| 541 | TNSRLRHCAY | RCYATWRFGS | QDMADFAILP | SCCRWRIRKE | FPKSEGQYSG | FKSPY |

Figure 2

HUMAN P2X$_1$

1    MARRFQEELA AFLFEYDTPR MVLVRNKKVG VIFRLIQLVV LVYVIGWVFL YEKGYQTSSG

61   LISSVSVKLK GLAVTQLPGL GPQVWDVADY VFPAQGDNSF VVMTNFIVTP KQTQGYCAEH

121  PEGGICKEDS GCTPGKAKRK AQGIRTGKCV AFNDTVKTCE IFGWCPVEVD DDIPRPALLR

181  EAENFTLFIK NSISFPRFKV NRRNLVEEVN AAHMKTCLFH KTLHPLCPVF QLGYVVQESG

241  QNFSTLAEKG GVVGITIDWH CDLDWHVRHC RPIYEFHGLY EEKNLSPGFN FRFARHFVEN

301  GTNYRHLFKV FGIRFDILVD GKAGKFDIIP TMTTIGSGIG IFGVATVLCD LLLLHILPKR

361  HYYKQKKFKY AEDMGPGAAE RDLAATSSTL GLQENMRTS

Figure 3

HUMAN P2X$_2$

| | | | | | |
|---|---|---|---|---|---|
| 1 | MAAAQPKYPA | GATARRLARG | CWSALWDYET | PKVIVVRNRR | LGVLYRAVQL | LILLYFVWYV |
| 61 | FIVQKSYQES | ETGPESSIIT | KVKGITTSEH | KVWDVEEYVK | PPEGGSVFSI | ITRVEATHSQ |
| 121 | TQGTCPESIR | VHNATCLSDA | DCVAGELDML | GNGLRTGRCV | PYYQGPSKTC | EVFGWCPVED |
| 181 | GASVSQFLGT | MAPNFTILIK | NSIHYPKFHF | SKGNIADRTD | GYLKRCTFHE | ASDLYCPIFK |
| 241 | LGFIVEKAGE | SFTELAHKGG | VIGVIINWDC | DLDLPASECN | PKYSFRRLDP | KHVPASSGYN |
| 301 | FRFAKYYKIN | GTTTRTLIKA | YGIRIDVIVH | GQAGKFSLIP | TIINLATALT | SVGVVRNPLW |
| 361 | GPSGCGGSTR | PLHTGLCWPQ | GSFLCDWILL | TFMNKNKVYS | HKKFDKVCTP | SHPSGSWPVT |
| 421 | LARVLGQAPP | EPGHRSEDQH | PSPPSGQEGQ | QGAECGPAFP | PLRPCPISAP | SEQMVDTPAS |
| 481 | EPAQASTPTD | PKGLAQL | | | | |

Figure 4

HUMAN P2X3

| | |
|---|---|
| 1 | MNCISDFFTY ETTKSVVVKS WTIGIINRVV QLLIISYFVG WVFLHEKAYQ VRDTAIESSV |
| 61 | VTKVKGSGLY ANRVMDVSDY VTPPQGTSVF VIITKMIVTE NQMQGFCPES EEKYRCVSDS |
| 121 | QCGPEPLPGG GILTGRCVNY SSVLRTCEIQ GWCPTEVDTV ETPIMMEAEN FTIFIKNSIR |
| 181 | FPLFNFEKGN LLPNLTARDM KTCRFHPDKD PFCPILRVGD VVKFAGQDFA KLARTGGVLG |
| 241 | IKIGWVCDLD KAWDQCIPKY SFTRLDSVSE KSSVSPGYNF RFAKYYKMEN GSEYRTLLKA |
| 301 | NETTLKIAA LTNPVYPSDQ TTAEKQSTDS GAFSIGH |

Figure 5

HUMAN P2X₄

| | | | | | |
|---|---|---|---|---|---|
| 1 | MAGCCAALAA | FLFEYDTPRI | VLIRSRKVGL | MNRAVQLLIL | AYVIGWVFVW EKGYQETDSV |
| 61 | VSSVTTKVKG | VAVTNTSKLG | FRIWDVADYV | IPAQEENSLF | VMTNVILTMN QTQGLCPEIP |
| 121 | DATTVCKSDA | SCTAGSAGTH | SNGVSTGRCV | AFNGSVKTCE | VAAWCPVEDD THVPQPAFLK |
| 181 | AAENFTLLVK | NNIWYPKFNF | SKRNILPNIT | TTYLKSCIYD | AKTDPFCPIF RLGKIVENAG |
| 241 | HSFQDMAVEG | GIMGIQVNWD | CNLDRAASLC | LPRYSFRRLD | TRDVEHNVSP GYNFRFAKYY |
| 301 | RDLAGNEQRT | LIKAYGIRFD | IIVFGKAGKF | DIIPTMINIG | SGLALLGMAT VLCDIIVLYC |
| 361 | MKKRLYYREK | KYKYVEDYEQ | GLASELDQ | | |

Figure 6

HUMAN P2X₅

| | | | | | |
|---|---|---|---|---|---|
| 1 | MGQAGCKGLC | LSLFDYKTEK | YVIAKNKKVG | LLYRLLQASI | LAYLVVWVFL | IKKGYQDVDT |
| 61 | SLQSAVITKV | KGVAFTNTSD | LGQRIWDVAD | YVIPAQGENV | FFVVTNLIVT | PNQRQNVCAE |
| 121 | NEGIPDGACS | KDSDCHAGEA | VTAGNGVKTG | RCLRRGNLAR | GTCEIFAWCP | LETSSRPEEP |
| 181 | FLKEAEDFTI | FIKNHIRFPK | FNFSKNNVMD | VKDRSFLKSC | HFGPKNHYCP | IFRLGSIVRW |
| 241 | AGSDFQDIAL | RGGVIGINIE | WNCDLDKAAS | ECHPHYSFSR | LDNKLSKSVS | SGYNFRFARY |
| 301 | YRDAAGVEFR | TLMKAYGIRF | DVMVNGKGAF | FCDLVLIYLI | KKREFYRDKK | YEEVRGLEDS |
| 361 | SQEAEDEASG | LGLSEQLTSG | PGLLGMPEQQ | ELQEPPEAKR | GSSSQKGNGS | VCPQLLEPHR |
| 421 | ST |

Figure 7

HUMAN P2X₆

| | | | | | |
|---|---|---|---|---|---|
| 1 | MGSPGATTGW | GLLDYKTEKY | VMTRNWRVGA | LQRLLQFGIV | VYVVGWALLA KKGYQERDLE |
| 61 | PQFSIITKLK | GVSVTQIKEL | GNRLWDVADF | VKPPQGENVF | FLVTNFLVTP AQVQGRCPEH |
| 121 | PSVPLANCWV | DEDCPEGEGG | THSHGVKTGQ | CVVFNGTHRT | CEIWSWCPVE SGVVPSRPLL |
| 181 | AQAQNFTLFI | KNTVTFSKFN | FSKSNALETW | DPTYFKHCRY | EPQFSPYCPV FRIGDLVAKA |
| 241 | GGTFEDLALL | GGSVGIRVHW | DCDLDTGDSG | CWPHYSFQLQ | EKSYNFRTAT HWWEQPGVEA |
| 301 | RTLLKLYGIR | FDILVTGQAG | KFGLIPTAVT | LGTGAAWLGV | VTFFCDLLLL YVDREAHFYW |
| 361 | RTKYEEAKAP | KATANSVWRE | LALASQARLA | ECLRRSSAPA | PTATAAGSQT QTPGWPCPSS |
| 421 | DTHLPTHSGS L | | | | |

Figure 8

HUMAN ISOFORM H (MTPGDHSW + 99-595)

```
                              MTPGDHSWGN SFFVMTNFLK TEGQEQRLCP

121    EYPTRRTLCS SDRGCKKGWM DPQSKGIQTG RCVVHEGNQK TCEVSAWCPI EAVEEAPRPA

181    LLNSAENFTV LIKNNIDFPG HNYTTRNILP GLNITCTFHK TQNPQCPIFR LGDIFRETGD

241    NFSDVAIQGG IMGIEIYWDC NLDRWFHHCR PKYSFRRLDD KTTNVSLYPG YNFRYAKYYK

301    ENNVEKRTLI KVFGIRFDIL VFGTGGKFDI IQLVVYIGST LSYFGLAAVF IDFLIDTYSS

361    NCCRSHIYPW CKCCQPCVVN EYYYRKKCES IVEPKPTLKY VSFVDESHIR MVNQQLLGRS

421    LQDVKGQEVP RPAMDFTDLS RLPLALHDTP PIPGQPEEIQ LLRKEATPRS RDSPVWCQCG

481    SCLPSQLPES HRCLEELCCR KKPGACITTS ELFRKLVLSR HVLQFLLLYQ EPLLALDVDS

541    TNSRLRHCAY RCYATWRFGS QDMADFAILP SCCRWRIRKE FPKSEGQYSG FKSPY
```

Figure 9

HUMAN ISOFORM D (MDGPAEQ + 178-595)

```
                                                                    MDGPAEQRPA
181    LLNSAENFTV  LIKNNIDFPG  HNYTTRNILP  GLNITCTFHK  TQNPQCPIFR  LGDIFRETGD
241    NFSDVAIQGG  IMGIEIYWDC  NLDRWFHHCR  PKYSFRRLDD  KTTNVSLYPG  YNFRYAKYYK
301    ENNVEKRTLI  KVFGIRFDIL  VFGTGGKFDI  IQLVVYIGST  LSYFGLAAVF  IDFLIDTYSS
361    NCCRSHIYPW  CKCCQPCVVN  EYYYRKKCES  IVEPKPTLKY  VSFVDESHIR  MVNQQLLGRS
421    LQDVKGQEVP  RPAMDFTDLS  RLPLALHDTP  PIPGQPEEIQ  LLRKEATPRS  RDSPVWCQCG
481    SCLPSQLPES  HRCLEELCCR  KKPGACITTS  ELFRKLVLSR  HVLQFLLLYQ  EPLLALDVDS
541    TNSRLRHCAY  RCYATWRFGS  QDMADFAILP  SCCRWRIRKE  FPKSEGQYSG  FKSPY
```

Figure 10

HUMAN ISOFORM RECEPTOR B (1-346 + VRDSEGSD)

```
1    MPACCSCSDV FQYETNKVTR IQSMNYGTIK WFFHVIIFSY VCFALVSDKL YQRKEPVISS

61   VHTKVKGIAE VKEEIVENGV KKLVHSVFDT ADYTFPLQGN SFFVMTNFLK TEGQEQRLCP

121  EYPTRRTLCS SDRGCKKGWM DPQSKGIQTG RCVVHEGNQK TCEVSAWCPI EAVEEAPRPA

181  LLNSAENFTV LIKNNIDFPG HNYTTRNILP GLNITCTFHK TQNPQCPIFR LGDIFRETGD

241  NFSDVAIQGG IMGIEIYWDC NLDRWFHHCR PKYSFRRLDD KTTNVSLYPG YNFRYAKYYK

301  ENNVEKRTLI KVFGIRFDIL VFGTGGKFDI IQLVVYIGST LSYFGLVRDS EGSD
```

Figure 11

HUMAN ISOFORM F RECEPTOR (MWQ + 293-595)

```
                                                              M WQFRYAKYYK

301    ENNVEKRTLI  KVFGIRFDIL  VFGTGGKFDI  IQLVVYIGST  LSYFGLAAVF  IDFLIDTYSS

361    NCCRSHIYPW  CKCCQPCVVN  EYYYRKKCES  IVEPKPTLKY  VSFVDESHIR  MVNQQLLGRS

421    LQDVKGQEVP  RPAMDFTDLS  RLPLALHDTP  PIPGQPEEIQ  LLRKEATPRS  RDSPVWCQCG

481    SCLPSQLPES  HRCLEELCCR  KKPGACITTS  ELFRKLVLSR  HVLQFLLLYQ  EPLLALDVDS

541    TNSRLRHCAY  RCYATWRFGS  QDMADFAILP  SCCRWRIRKE  FPKSEGQYSG  FKSPY
```

Figure 12

HUMAN ISOFORM E RECEPTOR (1-205 + 295-346 + VRDSLFHALGKWFGEGSD)

| | | | | | |
|---|---|---|---|---|---|
| 1 | MPACCSCSDV | FQYETNKVTR | IQSMNYGTIK | WFFHVIIFSY | VCFALVSDKL YQRKEPVISS |
| 61 | VHTKVKGIAE | VKEEIVENGV | KKLVHSVFDT | ADYTFPLQGN | SFFVMTNFLK TEGQEQRLCP |
| 121 | EYPTRRTLCS | SDRGCKKGWM | DPQSKGIQTG | RCVVHEGNQK | TCEVSAWCPI EAVEEAPRPA |
| 181 | LLNSAENFTV | LIKNNIDFPG | HNYTT | | |
| 241 | | | | | YAKYYK |
| 301 | ENNVEKRTLI | KVFGIRFDIL | VFGTGGKFDI | IQLVVYIGST | LSYFGLVRDS LFHALGKWFG |
| 361 | EGSD | | | | |

Figure 13

HUMAN ISOFORM G RECEPTOR (MTPGDHSW + 99-346 + VRDSLFHALGKWFGEGSD)

61                                              MTPGDHSWGN SFFVMTNFLK TEGQEQRLCP

121   EYPTRRTLCS SDRGCKKGWM DPQSKGIQTG RCVVHEGNQK TCEVSAWCPI EAVEEAPRPA

181   LLNSAENFTV LIKNNIDFPG HNYTTRNILP GLNITCTFHK TQNPQCPIFR LGDIFRETGD

241   NFSDVAIQGG IMGIEIYWDC NLDRWFHHCR PKYSFRRLDD KTTNVSLYPG YNFRYAKYYK

301   ENNVEKRTLI KVFGIRFDIL VFGTGGKFDI IQLVVYIGST LSYFGLVRDS LFHALGKWFG
361   EGSD

Figure 14

HUMAN ISOFORM J RECEPTOR (1-248 + IRQVLQGKQC)

| | |
|---|---|
| 1 | MPACCSCSDV FQYETNKVTR IQSMNYGTIK WFFHVIIFSY VCFALVSDKL YQRKEPVISS |
| 61 | VHTKVKGIAE VKEEIVENGV KKLVHSVFDT ADYTFPLQGN SFFVMTNFLK TEGQEQRLCP |
| 121 | EYPTRRTLCS SDRGCKKGWM DPQSKGIQTG RCVVHEGNQK TCEVSAWCPI EAVEEAPRPA |
| 181 | LLNSAENFTV LIKNNIDFPG HNYTTRNILP GLNITCTFHK TQNPQCPIFR LGDIFRETGD |
| 241 | NFSDVAIQIR QVLQGKQC |

Figure 15

HUMAN ISOFORM C RECEPTOR (1-121 + EFRPEGV)

```
1    MPACCSCSDV FQYETNKVTR IQSMNYGTIK WFFHVIIFSY VCFALVSDKL YQRKEPVISS

61   VHTKVKGIAE VKEEIVENGV KKLVHSVFDT ADYTFPLQGN SFFVMTNFLK TEGQEQRLCP

121  EEFRPEGV
```

PURINERGIC (P2X) RECEPTORS IN EXTRA-CELLULAR BODY FLUID

CROSS-REFERENCES TO RELATED APPLICATIONS

This application is a continuation of U.S. Ser. No. 12/677,795, filed Mar. 11, 2010, which is national stage of PCT/AU2008/001365, filed Sep. 12, 2008, (incorporated by reference in its entirety for all purposes), which claims priority to Australian patent application number 2007905017, filed Sep. 14, 2007.

FIELD OF THE INVENTION

The invention relates to purinergic (P2X) receptors, to detection of protein in extra-cellular body fluids and to antibodies for the diagnosis of a disease or condition, especially cancer.

BACKGROUND OF THE INVENTION

Purinergic (P2X) receptors are ATP-gated cation-selective channels. Each receptor is made up of three protein subunits or monomers. To date seven separate genes encoding P2X monomers have been identified: P2X1, P2X2, P2X3, P2X4, P2X5, P2X5, (FIGS. 2 to 7 respectively, herein), P2X7 (FIG. 1).

P2X7 receptors are of particular interest as the expression of these receptors is understood to be limited to cells having potential to undergo programmed cell death, such as thymocytes, dendritic cells, lymphocytes, macrophages and monocytes. Further, a P2X7 receptor containing one or more monomers having a cis isomerisation at Pro210 (according to FIG. 1), and which is devoid of ATP binding function is found on cells that are understood to be unable to undergo programmed cell death, such as preneoplastic cells and neoplastic cells in the form of many carcinomas and blood cancers.

At least 9 splice variants of P2X7 monomers are known to exist (FIGS. 8 to 15). These include variants having cytoplasmic N and C termini, 2 transmembrane spanning domains and an extra-cellular domain, and variants that have a cytoplasmic N terminus, transmembrane domain and a truncated extra-cellular domain of various lengths.

To date, P2X7 receptors have only been detected in the cytoplasm, the nucleus and anchored to the lipid bilayer of the cell surface membrane by one or more transmembrane spanning domains as discussed above.

SUMMARY OF THE INVENTION

In certain embodiments there is provided an isolated purinergic receptor, monomer or fragment thereof obtainable from an extra-cellular body fluid.

In another embodiment there is provided an immune complex formed from the binding of an anti purinergic receptor antibody or fragment thereof to a purinergic receptor, monomer or fragment thereof as described above.

In a further embodiment there is provided a complex formed from the binding of a purine to a purinergic receptor, monomer or fragment thereof as described above.

In still further embodiments there is provided an antibody or fragment thereof for binding to an epitope on an extra-cellular purinergic receptor, monomer or fragment thereof, the epitope not being found on a purinergic receptor, monomer or fragment thereof that is expressed on a cell surface membrane.

In certain embodiments there is provided a method for determining whether an extra-cellular body fluid contains a purinergic receptor, monomer or fragment thereof including:
  contacting an extra-cellular body fluid with an anti purinergic receptor antibody or fragment thereof in conditions for forming an immune complex, and
  detecting whether an immune complex has been formed, wherein the detection of an immune complex indicates that the fluid contains a purinergic receptor, monomer or fragment thereof.

In other embodiments there is provided a method for determining whether an individual has cancer, or is predisposed to cancer including the steps of:
  providing a sample of extra-cellular body fluid obtained from an individual in whom the presence or absence of cancer or predisposition thereto is to be determined;
  contacting the sample with an anti purinergic (P2X) receptor antibody or fragment thereof in conditions for forming an immune complex between a purinergic (P2X) receptor, monomer or fragment thereof in the extra-cellular body fluid in the sample and the antibody or fragment thereof; and
  detecting whether the immune complex has been formed, thereby determining whether the individual has a cancer or predisposition thereto.

In yet further embodiments there is provided a method for determining whether an individual has cancer, or is predisposed to cancer including the steps of:
  providing a sample in the form of a tissue biopsy including an extra-cellular body fluid, the sample being obtained from an individual in whom the presence or absence of cancer or predisposition thereto is to be determined;
  contacting the sample with an anti purinergic (P2X) receptor antibody or fragment thereof in conditions for forming an immune complex between a purinergic (P2X) receptor, monomer or fragment thereof, in or derived from, the extra-cellular body fluid in the sample and the antibody or fragment thereof; and
  detecting whether the immune complex has been formed, to determine whether the individual has or is predisposed to a cancer.

In yet further embodiments there is provided a method for determining whether an individual has cancer or is predisposed to cancer including the steps of:
  administering an anti purinergic (P2X) receptor antibody or fragment thereof to an individual in whom the presence or absence of cancer or predisposition thereto is to be determined in conditions for forming an immune complex between the antibody or fragment thereof and a purinergic (P2X) receptor, monomer or fragment thereof in the extra-cellular body fluid of the individual; and
  detecting whether the immune complex has been formed to determine whether the individual has a cancer or predisposition thereto.

In yet further embodiments there is provided a method for determining whether an individual has cancer or is predisposed to cancer including the steps of:
  providing a sample of extra-cellular body fluid obtained from an individual in whom the presence or absence of cancer or predisposition thereto is to be determined;
  applying the sample to a solid phase in conditions for fixing a purinergic (P2X) receptor, monomer or fragment thereof in the extra-cellular body fluid of the individual to the solid phase;
  contacting the solid phase with an anti purinergic (P2X) receptor antibody or fragment thereof in conditions for forming an immune complex between a purinergic (P2X) receptor, monomer or fragment thereof fixed to the solid phase and the antibody or fragment thereof; and detecting whether the immune complex has been formed, thereby determining whether the individual has cancer or predisposition thereto.

In yet further embodiments there is provided a kit or composition for determining whether an individual has cancer, or predisposed to cancer including:

an anti purinergic (P2X) receptor antibody or fragment thereof, and/or a purinergic receptor, monomer or fragment thereof as described above; and optionally a further antibody for binding to the antibody or fragment thereof or the purinergic receptor, monomer or fragment thereof;

written instructions for use of the kit in a method described above.

Examples of purinergic receptors are P2X receptors, especially those comprising a P2X1, P2X2, P2X3, P2X4, P2X5, P2X6, P2X7 monomer. In certain embodiments, the purinergic receptor is a P2X7 receptor, examples of which are discussed further below.

BRIEF DESCRIPTION OF THE DRAWINGS

FIG. 1: Human P2X7 (SEQ ID NO:8).
FIG. 2: Human P2X1 (SEQ ID NO:9).
FIG. 3: Human P2X2 (SEQ ID NO:10).
FIG. 4: Human P2X3 (SEQ ID NO:11).
FIG. 5: Human P2X4 (SEQ ID NO:12).
FIG. 6: Human P2X5 (SEQ ID NO:13).
FIG. 7: Human P2X6 (SEQ ID NO:14).
FIG. 8: Human isoform H (SEQ ID NO:15).
FIG. 9: Human isoform D (SEQ ID NO:16).
FIG. 10: Human isoform B receptor (SEQ ID NO:17).
FIG. 11: Human isoform F receptor (SEQ ID NO:18).
FIG. 12: Human isoform E receptor (SEQ ID NO:19).
FIG. 13: Human isoform G receptor (SEQ ID NO:20).
FIG. 14: Human isoform J receptor (SEQ ID NO:21).
FIG. 15: Human isoform C receptor (SEQ ID NO:22).

DETAILED DESCRIPTION OF THE EMBODIMENTS

Figure 16:
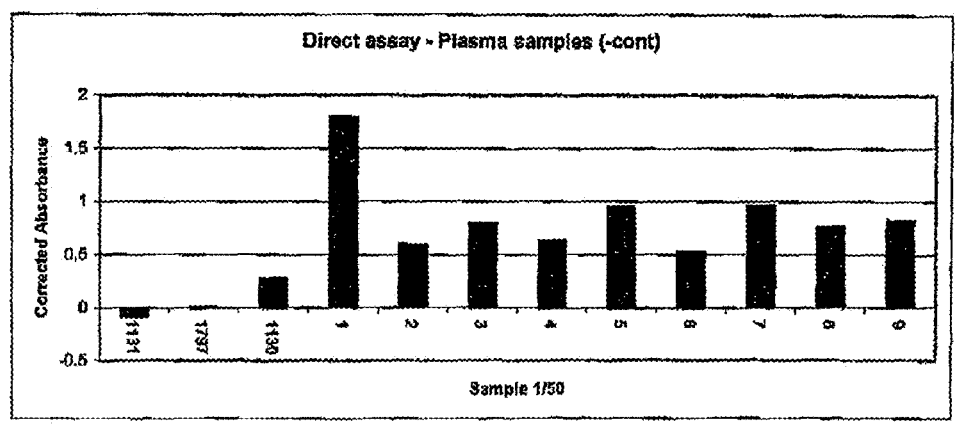
FIG. 16: Detection of (P2X) purinergic receptors in extracellular body fluid by direct ELISA.

The inventors have found purinergic (P2X) receptors in extracellular body fluids of individuals having various forms of cancer. This is a surprising finding as all P2X7 receptors to date have been found to be anchored into the cell surface lipid bilayer by one or two transmembrane spanning domains. Hence the teaching in the art to date has been that purinergic (P2X) receptors are expressed predominantly on the cell membrane.

The finding that certain purinergic (P2X) receptors are found in the extra-cellular body fluids of individuals having various disease and conditions, or predisposed to same is significant because in certain embodiments individuals may be screened on the basis of an extra-cellular body fluid sample, which is generally much more simple to isolate than a tissue biopsy. The latter has been required to determine cell membrane expression of purinergic P2X receptors to date.

In certain embodiments there is provided an isolated purinergic (P2X) receptor, P2X monomer or fragment thereof obtainable from an extra-cellular body fluid. Typically the receptor is a P2X7 receptor, monomer or fragment thereof.

In certain embodiments, a P2X7 receptor includes all receptors including at least one P2X7 monomer sequence, whether or not the P2X7 receptor is functional in the sense of capable of binding to ATP and or forming a pore for ingress of cations into a cell leading to programmed cell death. An example of a P2X7 receptor that has impaired ATP binding function is a receptor having a cis isomerisation at proline 210 of the sequence shown in SEQ ID NO: 1.

The fluid may be selected from the group consisting of blood, plasma, serum, lymph, urine, semen, saliva, sputum, ascites, faeces, uterine and vaginal secretions, bile, amniotic fluid, cerebrospinal fluid and organ and tissue flushings. The extra-cellular body fluid is typically cell-free although in some circumstances it may contain residual cells or fragments thereof.

The receptor, monomer or fragment thereof may include an amino acid sequence as shown in Table 1 below.

The receptor, monomer or fragment thereof may have an amino acid sequence consisting of part of any one of the sequences listed in Table 1. Typically a fragment is part of a monomer of at least about 10 amino acid residues length and no more than about 595 amino acids in length.

TABLE 1

| Name (SEQ ID NO:) | Accession no | Length (aa) |
|---|---|---|
| Human P2X7 isoform H (SEQ ID NO: 15) | AAX82093 | 505aa |
| Human P2X7 isoform D (SEQ ID NO: 16) | AAX82089 | 425aa |
| Human P2X7 isoform B (SEQ ID NO: 17) | AAX82087 | 364aa |
| Human P2X7 isoform F (SEQ ID NO: 18) | AAX82091 | 306aa |
| Human P2X7 isoform J (SEQ ID NO: 21) | ABD59798 | 258aa |
| Human P2X7 isoform E split splice (SEQ ID NO: 19) | AAX82090 | 275aa |
| Human P2X7 isoform C (SEQ ID NO: 22) | Q4VK13 | 128aa |
| Human P2X7 isoform G (SEQ ID NO: 20) | AAX82092 | 274aa |

The receptor, monomer or fragment thereof may have a molecular weight in the range of from 20 to 80 kDa.

The receptor, monomer or fragment thereof may lack a transmembrane domain.

The receptor, monomer or fragment thereof may be linked to a fragment of a cell membrane. The cell membrane fragment may be the result of cell lysis or membrane blebbing. The cell membrane fragment may be provided in the form of a liposome-like or micelle-like structure with purinergic (P2X) receptors located thereon.

In certain embodiments the receptor is linked to a solid phase, such as an assay plate, bead or tissue culture vessel. These forms of the receptor are particularly useful for preparation of antibodies to the receptor described further below which may be used in the diagnostic and therapeutic applications described further below.

In another embodiment there is provided an immune complex formed from the binding of an anti purinergic (P2X) receptor antibody or fragment thereof to a purinergic (P2X) receptor, monomer or fragment thereof as described above.

Generally an immune complex otherwise known as an antigen-antibody complex is a product that is formed from the binding of an antibody via an antibody binding site to an epitope on a antigen against which the antibody was raised. The complex may or may not consist of more than one antibody.

Typically the receptor is a P2X7 receptor and the antibody is an anti P2X7 antibody or fragment thereof.

The antibody may bind to an extra-cellular domain of a purinergic (P2X) receptor. In one embodiment, the purinergic (P2X) receptor is a P2X7 receptor. As discussed herein, there are a number of isoforms of the P2X7 receptor. The antibody may bind to any one of the domains of these isoforms. A full length isoform includes an intra-cellular N-terminal domain, a transmembrane domain, an extra-cellular domain, a further transmembrane domain and a C-terminal intra-cellular domain.

Examples of epitopes located on an extra-cellular domain of a P2X7 receptor are set forth in Table 2.

TABLE 2

| Antibody name | Epitope | Epitope amino acid sequence | SEQ ID NO: |
|---|---|---|---|
| E80-P2X7 | 71-87 inclusive + GSG | VKEEIVENGVKKLVHSVGSGC | SEQ ID NO: 1 |
| E200-P2X7 | 200-216 inclusive | GHNYTTRNILPGLNITC | SEQ ID NO: 2 |
| E200L | 197-216 inclusive | DFPGHNYTTRNILPGLNITC | SEQ ID NO: 3 |
| E200T-P2X7 | 197-207C inclusive | DFPGHNYTTRNC | SEQ ID NO: 4 |
| mP2X7 | 200-216 inclusive | GHNYTTRNILPTMNGSC | SEQ ID NO: 5 |
| E140P2X7 | 137-152 | KGWMDPQSKGIQTGRC | SEQ ID NO: 6 |
| E300 | 297-314 | KYYKENNVEKRTLIKVFC | SEQ ID NO: 7 |

The immune complex is particularly important as detection of this in vitro or in vivo is indicative of presence of, or predisposition to a disease or condition including preneoplasia and neoplasia. These detection methods are described in more detail below.

As is generally understood in the art, neoplasia is literally new growth and usually refers to abnormal new growth or proliferation generally persisting in the absence of an original growth stimulus. Neoplasia may be benign or malignant.

Pre-neoplasia is generally a form of cellular growth or transformation preceding neoplasia. It may be characterised by hyperplasia and/or appearance of mitotic figures histologically without marked anaplasia or loss of cell differentiation. Pre-neoplastic tissue is sometimes found in regions adjacent to a tumour lesion.

The extra-cellular body fluid is typically cell-free although in some circumstances it may contain residual cells or fragments thereof. However, the immune complexes are predominantly formed from antibody binding to receptors, monomers or fragments thereof that are not located on a cell surface of an intact or whole cell, but rather to receptors, monomers or fragments thereof that are suspended or dissolved in the body fluid.

The antibody may be a whole antibody of any isoform. The antibody may be one obtained from monoclonal or polyclonal antisera. The antibody may be produced by hybridoma, or by recombinant expression. The antibody may be human or one formed by grafting CDRs onto a xenogeneic or allogeneic framework.

Where the antibody is an antibody fragment, the antibody fragment is selected from the group consisting of a dAb, Fab, Fd, Fv, F(ab')2, scFv and CDR.

The antibody or antibody fragment may be attached to a solid phase, such as a bead or a plate, or blotting paper, for example nitrocellulose paper, so that the immune complex is attached to a solid phase when formed. In this embodiment the antibody may function as a "capture" antibody.

Alternatively, a receptor or fragment thereof is attached to a solid phase.

The anti P2X7 receptor antibody may be labelled for detection of formation of the immune complex.

The immune complex may further include a further antibody or fragment thereof, for example for capture of the immune complex. The further antibody or fragment thereof may be bound to the anti P2X7 receptor antibody. Also the further antibody or fragment thereof may be bound to the receptor or fragment thereof.

The further antibody or fragment thereof may be bound to a solid phase such as a phase described above.

The further antibody or fragment thereof may be labelled for detection of formation of the immune complex. Examples of labels include fluorophores, dyes, isotopes etc.

As an alternative, a complex may be provided by contacting a purinergic (P2X) receptor, such as a P2X7 receptor to a compound capable of binding to the receptor to form a detectable complex.

Thus in a further embodiment them is provided a complex formed from the binding of a purine or purine related compound to a P2X7 receptor, monomer, or fragment thereof as described above. An example is ATP or ATP analogue such as benzoyl-benzoyl ATP. The ATP may be bound or conjugated to a label to facilitate detection of formation of the complex.

In still further embodiments there is provided an antibody or fragment thereof for binding to an epitope on an extracellular purinergic receptor, monomer or fragment thereof, the epitope not being found on a purinergic receptor, monomer or fragment thereof that is expressed on a cell surface membrane.

Typically the antibody binds to an epitope on an extra-cellular P2X7 receptor, monomer or fragment thereof.

An example of an antibody fragment includes a dAb, Fab, Fd, Fv, F(ab')2, scFv and CDR.

In certain embodiments there is provided a method for determining whether an extra-cellular body fluid contains a purinergic receptor, monomer or fragment thereof including:

contacting an extra-cellular body fluid with an anti purinergic receptor antibody or fragment thereof in conditions for forming an immune complex, and detecting whether an immune complex has been formed, wherein the detection of an immune complex indicates that the fluid contains a purinergic receptor, monomer or fragment thereof.

Typically the antibody is an anti purinergic (P2X) receptor antibody such as an anti P2X7 receptor antibody or, fragment thereof.

In other embodiments there is provided a use of an anti P2X7-receptor antibody or fragment thereof in the manufacture of means for determining whether an extra-cellular body fluid contains a P2X7 receptor, monomer or fragment thereof.

In other embodiments there is provided a method for determining whether an extra-cellular body fluid contains an antibody against an extra-cellular purinergic receptor, monomer or fragment thereof including:

contacting extra-cellular body fluid with a purinergic receptor, monomer or fragment thereof in conditions for forming an immune complex between the purinergic receptor, monomer or fragment thereof and an antibody against an extra-cellular purinergic receptor, and detecting whether an immune complex has been formed; wherein the detection of an immune complex indicates that the fluid contains an antibody against an extra-cellular purinergic receptor, monomer or fragment thereof.

Typically the purinergic P2X receptor is a P2X7 receptor, monomer or fragment thereof.

In other embodiments there is provided a use of a P2X7 receptor, monomer or fragment thereof obtainable from an extra-cellular body fluid in the manufacture of means for determining whether an extra-cellular body fluid contains an anti-P2X7 receptor antibody.

The presence of a given protein, or level of expression of a given protein such as a purinergic (P2X) receptor or fragment thereof in an extra-cellular body fluid can be detected by any number of assays. Examples include immunoassays, chromatography and mass spectrometry.

Immunoassays, i.e. assays involving an element of the immune system are particularly preferred. These assays may generally be classified into one of:

(i) assays in which purified antigen is used to detect an antibody In host serum. For example, purified antigen is bound to solid phase by adsorption or indirectly through another molecule and host serum or other body fluid is applied followed by another antibody for detecting presence or absence of host antibody;

(ii) assays in which purified antigen is used to detect immune cells, such as T and B lymphocytes. For example, peripheral white cells are purified from a host and cultured with purified antigen. The presence or absence of one or more factors indicating immunity are then detected. Other examples include assays that measure cell proliferation (lymphocyte proliferation or transformation assays) following exposure to purified antigen, and assays that measure cell death (including apoptosis) following exposure to purified antigen:

(iii) assays in which purified antibody specific for antigen is used to detect antigen in the host. For example, purified antibody is bound to solid phase, host extra-cellular body fluid is then applied followed by another antibody specific for the antigen to be detected. There are many examples of this approach including ELISA, RIA and the like;

(iv) assays in which a purified anti-idiotypic antibody is used to detect host antibody. For example, anti-idiotypic antibody is adsorbed to solid phase, host serum is added and anti-Fc antibody is added to bind to any host antibodies having been bound by the anti-idiotypic antibody.

(v) assays in which extra-cellular body fluid is separated from a protein component contained within it, the protein component is then fixed onto a solid phase and the probed with an antibody. Examples include dot blotting and Western blotting.

The immunoassays can be applied in vitro or in vivo.

A further assay format which does not require formation of an immune complex is one in which an assay output is the result of catalysis of a substrate and the output is observed for example by measuring a change in optical density.

The extra-cellular body fluid to be assessed in the above described embodiments of the invention may be selected from the group consisting of blood, plasma, serum, lymph, urine, semen, saliva, sputum, ascites, faeces, uterine and vaginal secretions, bile, amniotic fluid, cerebrospinal fluid, tear, and organ and tissue flushings. The extra-cellular body fluid is typically cell-free although in some circumstances it may contain residual cells or fragments thereof.

It will be appreciated that any disease where a purinergic (P2X) receptor is expressed in extra-cellular body fluid can be detected by these methods. The disease is typically a cancer such as carcinoma, sarcoma, lymphoma, leukaemia or other parenchymal cell growth abnormality.

Carcinomas that may be detected include, but not limited to, prostate, breast, skin, lung, cervix, uterus, stomach, esophagus, bladder, and colon cancers. As generally understood, a cancer or tumour is a neoplastic state and may be benign or malignant. In certain embodiments the cancer is metastatic disease.

Whilst any body fluid can be used to detect any of these diseases, in certain embodiments, some body fluids may be more appropriate than others to detect certain diseases, for example urine may be more appropriate to detect prostate cancer. Blood may be more appropriate for detecting blood cancers such as lymphoma.

In another embodiment there is provided a method for determining whether an individual has a cancer including the steps of:

collecting a sample of extra-cellular body fluid from the individual and contacting extra-Cellular body fluid with an anti purinergic (P2X) receptor antibody or fragment thereof in conditions for forming an immune complex as described above, and detecting whether an immune complex has been formed.

In a further embodiment there is provided use of anti purinergic (P2X) receptor antibody or fragment thereof for determining whether an individual has a cancer.

In yet further embodiments there is provided a method for determining whether an individual has cancer, or is predisposed to cancer including the steps of:

providing a sample of extra-cellular body fluid obtained from an individual in whom the presence or absence of cancer or predisposition thereto is to be determined;

contacting the sample with an anti purinergic (P2X) receptor antibody or fragment thereof in conditions for forming an immune complex (as described above) between a purinergic (P2X) receptor, monomer or fragment thereof in the extra-cellular body fluid in the sample and the antibody or fragment thereof; and detecting whether the immune complex has been formed, thereby determining whether the individual has a cancer or predisposition thereto.

In one embodiment the method is implemented as a direct, indirect or sandwich ELISA, RIA or like assay involving the application of a liquid sample to an assay system. The sample may or may not be processed prior to contact with an antibody.

In yet further embodiments there is provided a method for determining whether an individual has cancer, or is predisposed to cancer including the steps of:

providing a sample in the form of a tissue biopsy including an extra-cellular body fluid, the sample being obtained from an individual in whom the presence or absence of cancer or predisposition thereto is to be determined;

contacting the sample with an anti purinergic (P2X) receptor antibody or fragment thereof in conditions for forming an immune complex between a purinergic (P2X) receptor, monomer or fragment thereof, in or derived from, the extra-cellular body fluid in the sample and the antibody or fragment thereof; and detecting whether the immune complex has been formed, to determine whether the individual has or is predisposed to a cancer.

In one embodiment the method is implemented in an immuno-histochemical format whereby a tissue section containing extra-cellular body fluid is applied to a slide leading to fixing of protein in the fluid to the slide and staining with an antibody. According to these embodiments, the method includes the step of assessing the sample, for example the tissue section, for the presence or absence of the immune complex in an extra-cellular space. Examples of these spaces include those in the form of a lumen of a gland, duct or vessel such as a blood vessel or lymphatic. Other extra-cellular spaces include those defined by an impermeable or semi-permeable layer of epithelial cells, one example of the former being the space defined by the blood brain barrier, an example of the latter being a convoluted tubule of a nephron.

In yet further embodiments there is provided a method for determining whether an individual has cancer or is predisposed to cancer including the steps of:

administering an anti purinergic (P2X) receptor antibody or fragment thereof to an individual in whom the presence or absence of cancer or predisposition thereto is to be determined in conditions for forming an immune complex between the antibody or fragment thereof and a purinergic (P2X) receptor, monomer or fragment thereof in the extra-cellular body fluid of the individual; and detecting whether the immune complex has been formed to determine whether the individual has a cancer or predisposition thereto.

The method may include the step of obtaining a sample of extra-cellular body fluid from the individual and determining whether the sample contains the immune complex, to detect whether the immune complex has been formed.

Alternatively, the method may include the step of obtaining a sample in the form of a tissue biopsy including an extra-cellular body fluid from the individual and assessing the sample for the presence or absence of the immune complex in an extra-cellular space of the tissue biopsy, to detect whether the immune complex has been formed.

In yet further embodiments there is provided a method for determining whether an individual has cancer or is predisposed to cancer including the steps of:

providing a sample of extra-cellular body fluid obtained from an individual in whom the presence or absence of cancer or predisposition thereto is to be determined;

applying the sample to a solid phase in conditions for fixing a purinergic (P2X) receptor, monomer or fragment thereof in the extra-cellular body fluid of the individual to the solid phase;

contacting the solid phase with an anti purinergic (P2X) receptor antibody or fragment thereof in conditions for forming an immune complex between a purinergic (P2X) receptor, monomer or fragment thereof fixed to the solid phase and the antibody or fragment thereof; and detecting whether the immune complex has been formed, thereby determining whether the individual has cancer or predisposition thereto.

In yet further embodiments there is provided a kit or composition for determining whether an extra-cellular body fluid contains a purinergic (P2X) receptor, monomer of fragment thereof as described above, or an antibody against an extra-cellular P2X7 receptor or fragment thereof as described above including:

an anti purinergic (P2X) receptor antibody or fragment thereof; and/or a P2X7 receptor, monomer or fragment thereof obtainable from extra-cellular body fluid as described above; and optionally a further antibody for binding to the antibody or fragment thereof or the P2X7 receptor, monomer or fragment thereof;

written instructions for use of the kit in a method described above.

EXAMPLES

The following protocols are provided as non-limiting examples of suitable methods for detecting P2X7R in a sample of extra-cellular fluid for the purpose of illustrating the invention.

Example 1

Detection of (P2X) purinergic receptors in extra-cellular body fluid by direct ELISA. Plasma samples (1 mL) obtained from 9 patients with Grade III ovarian adenocarcinoma were diluted 1:50 for direct ELISA in triplicate. Control plasma are the 3 samples at left (FIG. 16).

Only low volumes of samples were required for reliable detection of shed receptor sourced from cancer cells in the patients' plasma.

Example 2

Figure 17:
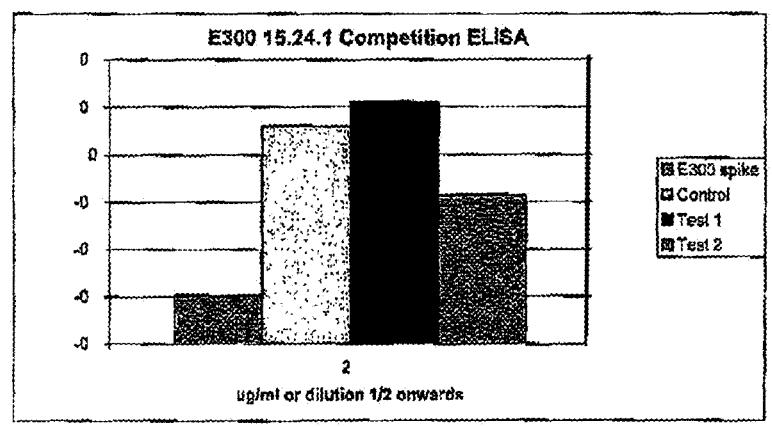
FIG. 17: Detection of (P2X) purinergic receptors in extracellular body fluid by indirect ELISA.

Detection of (P2X) purinergic receptors in extra-cellular body fluid by indirect ELISA. Shed receptor from bladder cancer patients was detected in urine. Patients with extant disease and those in remission following treatment could be separated using a competition ELISA. Urine was diluted 1:10 and the spiked P2X7 antibody was used at 2.5 ug/mL (FIG. 17). Test sample 1 was a patient in remission, close to the control level, while Test sample 2 had existing disease manifest by the presence of shed receptor. Urine samples (1 mL) were sufficient for detection (in triplicate).

Example 3

Detection of (P2X) Purinergic Receptors in Extra-Cellular Body Fluid by Dot Blotting.

Samples of urine from patients with ovarian and bladder cancer were examined using dot blots and a range of antibodies to P2X7 receptors. PVDF sheets were wet in PBS for 15 min then air dried. Sheets were then dotted with urine or sera (neat or diluted) and dried at 37 C. Sheets were then placed at 4 C (dry) until ready to test.

Sheets were wet in TBS before blocking in 3% BSA/TBS for 1 hr.

Antibodies were added into bags containing nitrocellulose sheets (1 sheet per bag) at 50 ug/mL in 3% BSA/TBS and incubated on rocker for 2 hrs.

Sheets were washed three times in TBS before conjugates were added at 1/1K concentration in 3% BSA/TBS and placed on rocker for 1.5 hrs.

Sheets were washed in TBS for 4 solution changes then developed using Chloro-1-Napthol.

Staining was neutralized in tap water before air drying and photographing with video camera.

Figure 18:
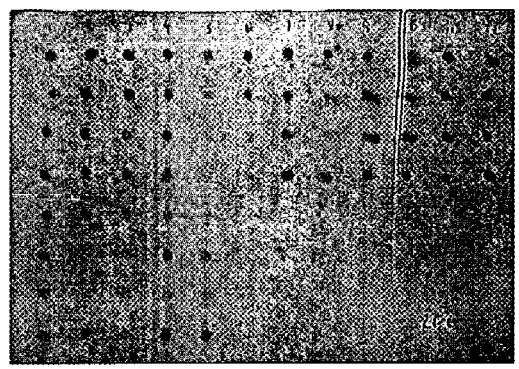
FIG. 18: Dot blot obtained with urine from ovarian and bladder cancer patients as well as controls.

FIG. 18 is an example of results obtained with ovarian and bladder cancer patients as well as controls. Urine from all cancer positive patients was observed to contain P2X7 while the control urine samples were devoid of detectable levels of receptor.

Example 4

Figure 19A:
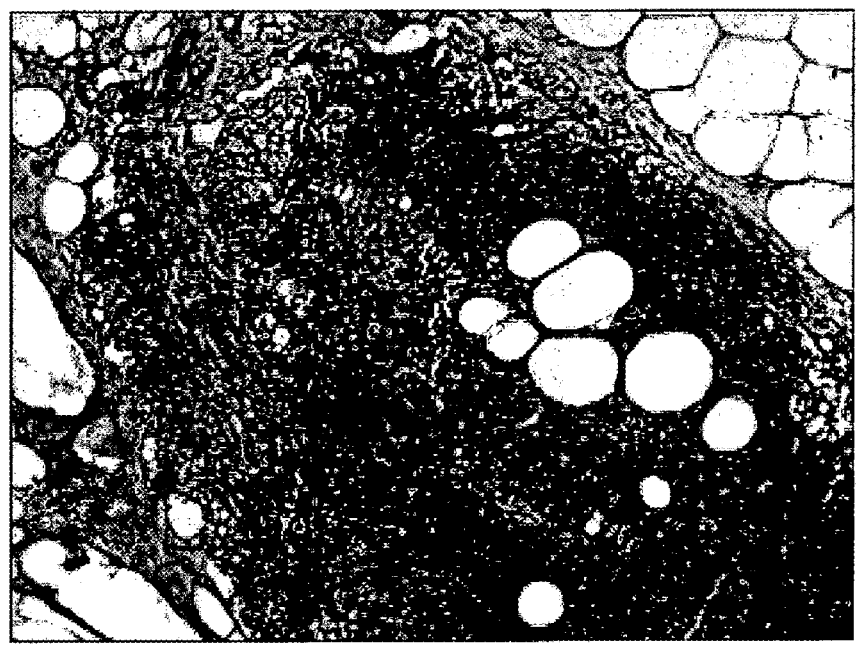
FIG. 19A: Immunohistochemistry for non-functional P2X7 receptor in sentinel lymph nodes from prostate cancer.
Figure 19B:
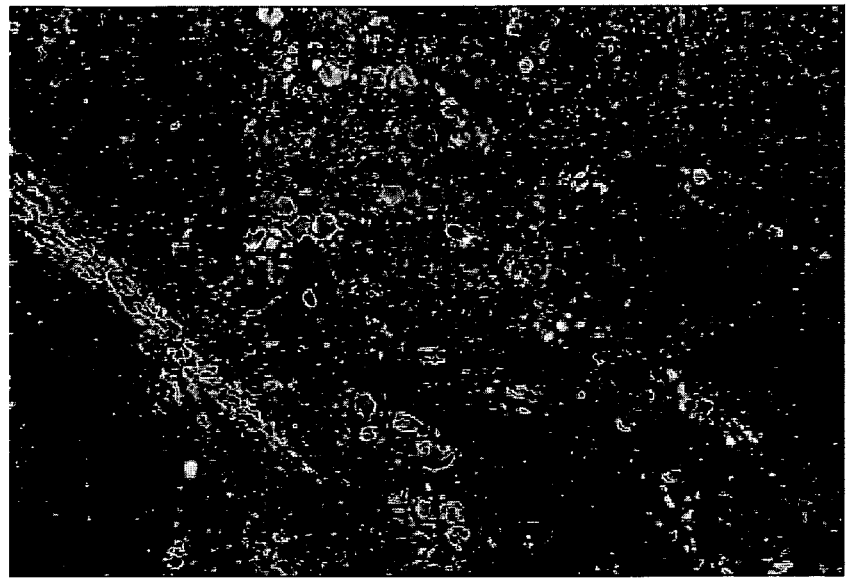
FIG. 19B: Immunohistochemistry for non-functional P2X7 receptor in sentinel lymph nodes from breast cancer.
Figure 19C:
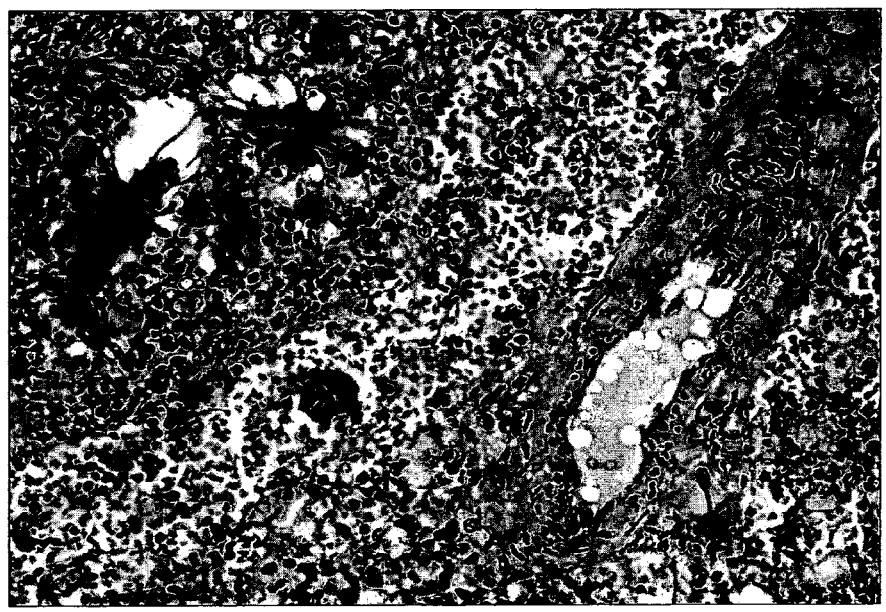
FIG. 19C: Immunohistochemistry for non-functional P2X7 receptor in lymph nodes.
Figure 20:
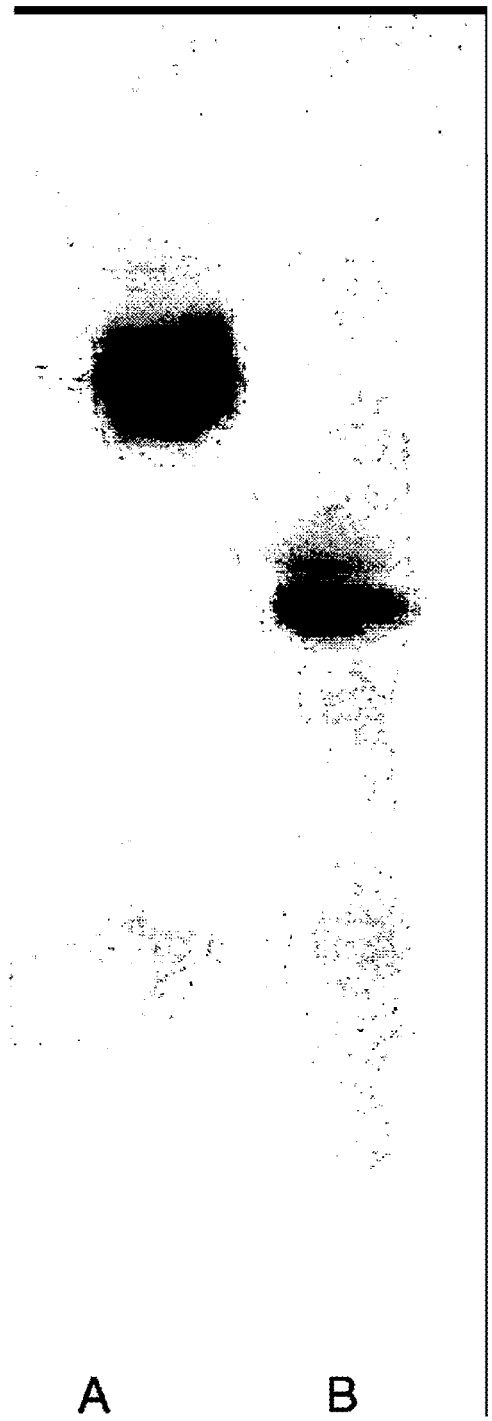
FIG. 20: Western Blot of faecal samples.

Detection of (P2X) purinergic receptors in extra-cellular body fluid by immuno histochemistry. In one embodiment of the invention we have detected shed receptor in lymph nodes draining the area of identified tumours. In the absence of metastatic cells, lymph nodes considered sentinel nodes for breast and prostate cancers were removed in the course of surgery, fixed and embedded. Sections were stained for the presence of non-functional P2X7 receptor. Receptor was detected in the sentinel nodes whereas control nodes were devoid of shed receptor in the medulla. Examples, include prostate (A) and breast (B) where brown stain in the form of DAB reveals the presence of receptor, (FIG. 19).

Example 5

Detection of Prostate Cancer by Detection of (P2X) Purinergic Receptors in Serum and Urine.

In one embodiment of the invention we have used a direct ELISA to detect the presence of P2X7 receptor in urine and serum from a patient with advanced prostate cancer.

The microtitre plate-based EIA kit consists of 12 strips of 8 wells each, pre-coated with E80, E140 or E200 antibodies to P2X7. The assay operates on the basis of competition between the shed receptor in the sample and the receptor-enzyme conjugate for the limited number of specific binding sites on the pre-coated microtitre plate.

After overnight incubation, unbound reagents were removed by rinsing wells with PBS. The enzyme conjugate utilised horseradish peroxidase (HRP) as a tracer. The amount of P2X7-HRP bound was measured by adding the chromogen substrate 2,2'-azino-bis(3-ethylbenzthiazoline-6-sulfonic acid) diammonium salt (ARTS). Bound P2X7-HRP conjugate converted the colourless ABTS solution to a blue product. The ABTS reaction was stopped by the addition of the stopping solution, 5% oxalic acid, which converted the solution to a yellow-coloured product. The colour intensity was measured at 405 nm with reference at 490 nm using a microplate reader. The colour intensity was inversely proportional to the P2X7 epitope concentration in the calibrator or sample.

Example 6

Detection of Colon Cancer by Detection of (P2X) Purinergic Receptors in Faeces.

Faecal samples from two patients with established adenocarcinomas were collected and shed cells buffer extracted. The samples were run on polyacrylamide gels and major P2X7 protein bands identified in a Western blot. The figure shows two major bands at molecular weights of 75 kDa and 30 kDa respectively using an antibody to SEQ ID NO:2 corresponding with full length receptor and a truncated piece of receptor containing the epitope 200-216.

The invention claimed is:

1. A method for determining whether an individual has cancer, including the steps of:
    providing a sample in the form of a tissue biopsy, the biopsy including extracellular spaces that have extracellular body fluid contained therein;
    applying the sample to a slide or support, thereby enabling fixing of protein in extracellular fluid in the extra-cellular spaces to the slide or support;
    contacting the sample with an anti-P2X7 receptor antibody or fragment thereof that binds a P2X7 receptor comprising SEQ ID NO: 2 in conditions for forming an immune complex between a P2X7 receptor, monomer or fragment thereof, in or derived from the extracellular body fluid in the sample and the antibody or fragment thereof;
    assessing the sample for the presence or absence of an immune complex in an extracellular space of the sample; and
    determining that the individual has cancer wherein the assessment reveals the presence of immune complex in extracellular space.

2. The method of claim 1 wherein the extra-cellular space is in the form of a lumen of a gland, duct, vessel, tubule or blood brain barrier.

3. The method of claim 1 wherein the antibody or fragment thereof is a monoclonal antibody or fragment thereof.

4. The method of claim 1 wherein the antibody is attached to a label for the detection of the formation of the immune complex.

* * * * *

UNITED STATES PATENT AND TRADEMARK OFFICE
CERTIFICATE OF CORRECTION

PATENT NO. : 8,658,385 B2
APPLICATION NO. : 13/626833
DATED : February 25, 2014
INVENTOR(S) : Angus Gidley-Baird et al.

Page 1 of 1

It is certified that error appears in the above-identified patent and that said Letters Patent is hereby corrected as shown below:

Title page,

"Related U.S. Application Data

(63) Continuation of application No. 12/677,795,
  filed as application No. PCT/CT2008/001365 on Sep. 12, 2008,
  now Pat. No. 8,293,491."

should read

-- Related U.S. Application Data

(63) Continuation of application No. 12/677,795,
  filed as application No. PCT/AU2008/001365 on Sep. 12, 2008,
  now Pat. No. 8,293,491. --

Signed and Sealed this
Twenty-seventh Day of May, 2014

Michelle K. Lee
*Deputy Director of the United States Patent and Trademark Office*

SEQUENCE LISTING

```
<160> NUMBER OF SEQ ID NOS: 22

<210> SEQ ID NO 1
<211> LENGTH: 21
<212> TYPE: PRT
<213> ORGANISM: Homo sapiens

<400> SEQUENCE: 1

Val Lys Glu Glu Ile Val Glu Asn Gly Val Lys Lys Leu Val His Ser
1               5                   10                  15

Val Gly Ser Gly Cys
            20

<210> SEQ ID NO 2
<211> LENGTH: 17
<212> TYPE: PRT
<213> ORGANISM: Homo sapiens

<400> SEQUENCE: 2
```

-continued

Gly His Asn Tyr Thr Thr Arg Asn Ile Leu Pro Gly Leu Asn Ile Thr
1               5                   10                  15

Cys

<210> SEQ ID NO 3
<211> LENGTH: 20
<212> TYPE: PRT
<213> ORGANISM: Homo sapiens

<400> SEQUENCE: 3

Asp Phe Pro Gly His Asn Tyr Thr Thr Arg Asn Ile Leu Pro Gly Leu
1               5                   10                  15

Asn Ile Thr Cys
            20

<210> SEQ ID NO 4
<211> LENGTH: 12
<212> TYPE: PRT
<213> ORGANISM: Homo sapiens

<400> SEQUENCE: 4

Asp Phe Pro Gly His Asn Tyr Thr Thr Arg Asn Cys
1               5                   10

<210> SEQ ID NO 5
<211> LENGTH: 17
<212> TYPE: PRT
<213> ORGANISM: Homo sapiens

<400> SEQUENCE: 5

Gly His Asn Tyr Thr Thr Arg Asn Ile Leu Pro Thr Met Asn Gly Ser
1               5                   10                  15

Cys

<210> SEQ ID NO 6
<211> LENGTH: 16
<212> TYPE: PRT
<213> ORGANISM: Homo sapiens

<400> SEQUENCE: 6

Lys Gly Trp Met Asp Pro Gln Ser Lys Gly Ile Gln Thr Gly Arg Cys
1               5                   10                  15

<210> SEQ ID NO 7
<211> LENGTH: 18
<212> TYPE: PRT
<213> ORGANISM: Homo sapiens

<400> SEQUENCE: 7

Lys Tyr Tyr Lys Glu Asn Asn Val Glu Lys Arg Thr Leu Ile Lys Val
1               5                   10                  15

Phe Cys

<210> SEQ ID NO 8
<211> LENGTH: 595
<212> TYPE: PRT
<213> ORGANISM: Homo sapiens

<400> SEQUENCE: 8

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
                20                  25                  30

```
Phe His Val Ile Ile Phe Ser Tyr Val Cys Phe Ala Leu Val Ser Asp
            35                  40                  45

Lys Leu Tyr Gln Arg Lys Glu Pro Val Ile Ser Ser Val His Thr Lys
 50                  55                  60

Val Lys Gly Ile Ala Glu Val Lys Glu Glu Ile Val Glu Asn Gly Val
 65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
                100                 105                 110

Gly Gln Glu Gln Arg Leu Cys Pro Glu Tyr Pro Thr Arg Arg Thr Leu
                115                 120                 125

Cys Ser Ser Asp Arg Gly Cys Lys Lys Gly Trp Met Asp Pro Gln Ser
                130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
                180                 185                 190

Lys Asn Asn Ile Asp Phe Pro Gly His Asn Tyr Thr Thr Arg Asn Ile
                195                 200                 205

Leu Pro Gly Leu Asn Ile Thr Cys Thr Phe His Lys Thr Gln Asn Pro
                210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
                260                 265                 270

Tyr Ser Phe Arg Arg Leu Asp Asp Lys Thr Thr Asn Val Ser Leu Tyr
                275                 280                 285

Pro Gly Tyr Asn Phe Arg Tyr Ala Lys Tyr Tyr Lys Glu Asn Asn Val
                290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
                340                 345                 350

Phe Leu Ile Asp Thr Tyr Ser Ser Asn Cys Cys Arg Ser His Ile Tyr
                355                 360                 365

Pro Trp Cys Lys Cys Cys Gln Pro Cys Val Val Asn Glu Tyr Tyr Tyr
                370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
                420                 425                 430

Ala Met Asp Phe Thr Asp Leu Ser Arg Leu Pro Leu Ala Leu His Asp
                435                 440                 445

Thr Pro Pro Ile Pro Gly Gln Pro Glu Glu Ile Gln Leu Leu Arg Lys
```

```
                    450              455              460
Glu Ala Thr Pro Arg Ser Arg Asp Ser Pro Val Trp Cys Gln Cys Gly
465                 470              475                      480

Ser Cys Leu Pro Ser Gln Leu Pro Glu Ser His Arg Cys Leu Glu Glu
                485              490                  495

Leu Cys Cys Arg Lys Lys Pro Gly Ala Cys Ile Thr Thr Ser Glu Leu
                500              505              510

Phe Arg Lys Leu Val Leu Ser Arg His Val Leu Gln Phe Leu Leu Leu
            515              520              525

Tyr Gln Glu Pro Leu Leu Ala Leu Asp Val Asp Ser Thr Asn Ser Arg
        530              535              540

Leu Arg His Cys Ala Tyr Arg Cys Tyr Ala Thr Trp Arg Phe Gly Ser
545             550              555                      560

Gln Asp Met Ala Asp Phe Ala Ile Leu Pro Ser Cys Cys Arg Trp Arg
                565              570                  575

Ile Arg Lys Glu Phe Pro Lys Ser Glu Gly Gln Tyr Ser Gly Phe Lys
            580              585              590

Ser Pro Tyr
        595

<210> SEQ ID NO 9
<211> LENGTH: 399
<212> TYPE: PRT
<213> ORGANISM: Homo sapiens

<400> SEQUENCE: 9

Met Ala Arg Arg Phe Gln Glu Glu Leu Ala Ala Phe Leu Phe Glu Tyr
1               5                   10                  15

Asp Thr Pro Arg Met Val Leu Val Arg Asn Lys Lys Val Gly Val Ile
                20                  25                  30

Phe Arg Leu Ile Gln Leu Val Val Leu Val Tyr Val Ile Gly Trp Val
            35                  40                  45

Phe Leu Tyr Glu Lys Gly Tyr Gln Thr Ser Ser Gly Leu Ile Ser Ser
        50                  55                  60

Val Ser Val Lys Leu Lys Gly Leu Ala Val Thr Gln Leu Pro Gly Leu
65                  70                  75                  80

Gly Pro Gln Val Trp Asp Val Ala Asp Tyr Val Phe Pro Ala Gln Gly
                85                  90                  95

Asp Asn Ser Phe Val Val Met Thr Asn Phe Ile Val Thr Pro Lys Gln
                100                 105                 110

Thr Gln Gly Tyr Cys Ala Glu His Pro Glu Gly Gly Ile Cys Lys Glu
            115                 120                 125

Asp Ser Gly Cys Thr Pro Gly Lys Ala Lys Arg Lys Ala Gln Gly Ile
        130                 135                 140

Arg Thr Gly Lys Cys Val Ala Phe Asn Asp Thr Val Lys Thr Cys Glu
145                 150                 155                 160

Ile Phe Gly Trp Cys Pro Val Glu Val Asp Asp Ile Pro Arg Pro
                165                 170                 175

Ala Leu Leu Arg Glu Ala Glu Asn Phe Thr Leu Phe Ile Lys Asn Ser
            180                 185                 190

Ile Ser Phe Pro Arg Phe Lys Val Asn Arg Arg Asn Leu Val Glu Glu
        195                 200                 205

Val Asn Ala Ala His Met Lys Thr Cys Leu Phe His Lys Thr Leu His
    210                 215                 220

Pro Leu Cys Pro Val Phe Gln Leu Gly Tyr Val Val Gln Glu Ser Gly
```

```
                  225                 230                 235                 240

Gln Asn Phe Ser Thr Leu Ala Glu Lys Gly Gly Val Val Gly Ile Thr
                245                 250                 255

Ile Asp Trp His Cys Asp Leu Asp Trp His Val Arg His Cys Arg Pro
                260                 265                 270

Ile Tyr Glu Phe His Gly Leu Tyr Glu Lys Asn Leu Ser Pro Gly
                275                 280                 285

Phe Asn Phe Arg Phe Ala Arg His Phe Val Glu Asn Gly Thr Asn Tyr
                290                 295                 300

Arg His Leu Phe Lys Val Phe Gly Ile Arg Phe Asp Ile Leu Val Asp
305                 310                 315                 320

Gly Lys Ala Gly Lys Phe Asp Ile Ile Pro Thr Met Thr Thr Ile Gly
                325                 330                 335

Ser Gly Ile Gly Ile Phe Gly Val Ala Thr Val Leu Cys Asp Leu Leu
                340                 345                 350

Leu Leu His Ile Leu Pro Lys Arg His Tyr Tyr Lys Gln Lys Lys Phe
                355                 360                 365

Lys Tyr Ala Glu Asp Met Gly Pro Gly Ala Ala Glu Arg Asp Leu Ala
                370                 375                 380

Ala Thr Ser Ser Thr Leu Gly Leu Gln Glu Asn Met Arg Thr Ser
385                 390                 395

<210> SEQ ID NO 10
<211> LENGTH: 497
<212> TYPE: PRT
<213> ORGANISM: Homo sapiens

<400> SEQUENCE: 10

Met Ala Ala Ala Gln Pro Lys Tyr Pro Ala Gly Ala Thr Ala Arg Arg
1               5                   10                  15

Leu Ala Arg Gly Cys Trp Ser Ala Leu Trp Asp Tyr Glu Thr Pro Lys
                20                  25                  30

Val Ile Val Val Arg Asn Arg Arg Leu Gly Val Leu Tyr Arg Ala Val
                35                  40                  45

Gln Leu Leu Ile Leu Leu Tyr Phe Val Trp Tyr Val Phe Ile Val Gln
50                  55                  60

Lys Ser Tyr Gln Glu Ser Glu Thr Gly Pro Glu Ser Ser Ile Ile Thr
65                  70                  75                  80

Lys Val Lys Gly Ile Thr Thr Ser Glu His Lys Val Trp Asp Val Glu
                85                  90                  95

Glu Tyr Val Lys Pro Pro Glu Gly Gly Ser Val Phe Ser Ile Ile Thr
                100                 105                 110

Arg Val Glu Ala Thr His Ser Gln Thr Gln Gly Thr Cys Pro Glu Ser
                115                 120                 125

Ile Arg Val His Asn Ala Thr Cys Leu Ser Asp Ala Asp Cys Val Ala
                130                 135                 140

Gly Glu Leu Asp Met Leu Gly Asn Gly Leu Arg Thr Gly Arg Cys Val
145                 150                 155                 160

Pro Tyr Tyr Gln Gly Pro Ser Lys Thr Cys Glu Val Phe Gly Trp Cys
                165                 170                 175

Pro Val Glu Asp Gly Ala Ser Val Ser Gln Phe Leu Gly Thr Met Ala
                180                 185                 190

Pro Asn Phe Thr Ile Leu Ile Lys Asn Ser Ile His Tyr Pro Lys Phe
                195                 200                 205

His Phe Ser Lys Gly Asn Ile Ala Asp Arg Thr Asp Gly Tyr Leu Lys
```

```
                    210                 215                 220

Arg Cys Thr Phe His Glu Ala Ser Asp Leu Tyr Cys Pro Ile Phe Lys
225                 230                 235                 240

Leu Gly Phe Ile Val Glu Lys Ala Gly Glu Ser Phe Thr Glu Leu Ala
                    245                 250                 255

His Lys Gly Gly Val Ile Gly Val Ile Ile Asn Trp Asp Cys Asp Leu
                    260                 265                 270

Asp Leu Pro Ala Ser Glu Cys Asn Pro Lys Tyr Ser Phe Arg Arg Leu
                275                 280                 285

Asp Pro Lys His Val Pro Ala Ser Ser Gly Tyr Asn Phe Arg Phe Ala
290                 295                 300

Lys Tyr Tyr Lys Ile Asn Gly Thr Thr Thr Arg Thr Leu Ile Lys Ala
305                 310                 315                 320

Tyr Gly Ile Arg Ile Asp Val Ile Val His Gly Gln Ala Gly Lys Phe
                    325                 330                 335

Ser Leu Ile Pro Thr Ile Ile Asn Leu Ala Thr Ala Leu Thr Ser Val
                    340                 345                 350

Gly Val Val Arg Asn Pro Leu Trp Gly Pro Ser Gly Cys Gly Gly Ser
                    355                 360                 365

Thr Arg Pro Leu His Thr Gly Leu Cys Trp Pro Gln Gly Ser Phe Leu
370                 375                 380

Cys Asp Trp Ile Leu Leu Thr Phe Met Asn Lys Asn Lys Val Tyr Ser
385                 390                 395                 400

His Lys Lys Phe Asp Lys Val Cys Thr Pro Ser His Pro Ser Gly Ser
                    405                 410                 415

Trp Pro Val Thr Leu Ala Arg Val Leu Gly Gln Ala Pro Pro Glu Pro
                    420                 425                 430

Gly His Arg Ser Glu Asp Gln His Pro Ser Pro Ser Gly Gln Glu
                435                 440                 445

Gly Gln Gln Gly Ala Glu Cys Gly Pro Ala Phe Pro Pro Leu Arg Pro
                    450                 455                 460

Cys Pro Ile Ser Ala Pro Ser Glu Gln Met Val Asp Thr Pro Ala Ser
465                 470                 475                 480

Glu Pro Ala Gln Ala Ser Thr Pro Thr Asp Pro Lys Gly Leu Ala Gln
                    485                 490                 495

Leu

<210> SEQ ID NO 11
<211> LENGTH: 336
<212> TYPE: PRT
<213> ORGANISM: Homo sapiens

<400> SEQUENCE: 11

Met Asn Cys Ile Ser Asp Phe Phe Thr Tyr Glu Thr Thr Lys Ser Val
1               5                   10                  15

Val Val Lys Ser Trp Thr Ile Gly Ile Ile Asn Arg Val Val Gln Leu
                20                  25                  30

Leu Ile Ile Ser Tyr Phe Val Gly Trp Val Phe Leu His Glu Lys Ala
                35                  40                  45

Tyr Gln Val Arg Asp Thr Ala Ile Glu Ser Ser Val Val Thr Lys Val
            50                  55                  60

Lys Gly Ser Gly Leu Tyr Ala Asn Arg Val Met Asp Val Ser Asp Tyr
65                  70                  75                  80

Val Thr Pro Pro Gln Gly Thr Ser Val Phe Val Ile Ile Thr Lys Met
                85                  90                  95
```

```
Ile Val Thr Glu Asn Gln Met Gln Gly Phe Cys Pro Glu Ser Glu
            100                 105                 110

Lys Tyr Arg Cys Val Ser Asp Ser Gln Cys Gly Pro Glu Pro Leu Pro
115                 120                 125

Gly Gly Gly Ile Leu Thr Gly Arg Cys Val Asn Tyr Ser Ser Val Leu
130                 135                 140

Arg Thr Cys Glu Ile Gln Gly Trp Cys Pro Thr Glu Val Asp Thr Val
145                 150                 155                 160

Glu Thr Pro Ile Met Met Glu Ala Gly Asn Phe Thr Ile Phe Ile Lys
                165                 170                 175

Asn Ser Ile Arg Phe Pro Leu Phe Asn Phe Glu Lys Gly Asn Leu Leu
            180                 185                 190

Pro Asn Leu Thr Ala Arg Asp Met Lys Thr Cys Arg Phe His Pro Asp
            195                 200                 205

Lys Asp Pro Phe Cys Pro Ile Leu Arg Val Gly Asp Val Val Lys Phe
    210                 215                 220

Ala Gly Gln Asp Phe Ala Lys Leu Ala Arg Thr Gly Gly Val Leu Gly
225                 230                 235                 240

Ile Lys Ile Gly Trp Val Cys Asp Leu Asp Lys Ala Trp Asp Gln Cys
                245                 250                 255

Ile Pro Lys Tyr Ser Phe Thr Arg Leu Asp Ser Val Ser Glu Lys Ser
            260                 265                 270

Ser Val Ser Pro Gly Tyr Asn Phe Arg Phe Ala Lys Tyr Tyr Lys Met
        275                 280                 285

Glu Asn Gly Ser Glu Tyr Arg Thr Leu Leu Lys Ala Asn Glu Thr Thr
    290                 295                 300

Leu Lys Ile Ala Ala Leu Thr Asn Pro Val Tyr Pro Ser Asp Gln Thr
305                 310                 315                 320

Thr Ala Glu Lys Gln Ser Thr Asp Ser Gly Ala Phe Ser Ile Gly His
                325                 330                 335

<210> SEQ ID NO 12
<211> LENGTH: 388
<212> TYPE: PRT
<213> ORGANISM: Homo sapiens

<400> SEQUENCE: 12

Met Ala Gly Cys Cys Ala Ala Leu Ala Ala Phe Leu Phe Glu Tyr Asp
1               5                   10                  15

Thr Pro Arg Ile Val Leu Ile Arg Ser Arg Lys Val Gly Leu Met Asn
            20                  25                  30

Arg Ala Val Gln Leu Leu Ile Leu Ala Tyr Val Ile Gly Trp Val Phe
        35                  40                  45

Val Trp Glu Lys Gly Tyr Gln Glu Thr Asp Ser Val Val Ser Ser Val
50                  55                  60

Thr Thr Lys Val Lys Gly Val Ala Val Thr Asn Thr Ser Lys Leu Gly
65                  70                  75                  80

Phe Arg Ile Trp Asp Val Ala Asp Tyr Val Ile Pro Ala Gln Glu Glu
                85                  90                  95

Asn Ser Leu Phe Val Met Thr Asn Val Ile Leu Thr Met Asn Gln Thr
            100                 105                 110

Gln Gly Leu Cys Pro Glu Ile Pro Asp Ala Thr Thr Val Cys Lys Ser
        115                 120                 125

Asp Ala Ser Cys Thr Ala Gly Ser Ala Gly Thr His Ser Asn Gly Val
130                 135                 140
```

```
Ser Thr Gly Arg Cys Val Ala Phe Asn Gly Ser Val Lys Thr Cys Glu
145                 150                 155                 160

Val Ala Ala Trp Cys Pro Val Glu Asp Asp Thr His Val Pro Gln Pro
                165                 170                 175

Ala Phe Leu Lys Ala Ala Glu Asn Phe Thr Leu Leu Val Lys Asn Asn
            180                 185                 190

Ile Trp Tyr Pro Lys Phe Asn Phe Ser Lys Arg Asn Ile Leu Pro Asn
                195                 200                 205

Ile Thr Thr Thr Tyr Leu Lys Ser Cys Ile Tyr Asp Ala Lys Thr Asp
            210                 215                 220

Pro Phe Cys Pro Ile Phe Arg Leu Gly Lys Ile Val Glu Asn Ala Gly
225                 230                 235                 240

His Ser Phe Gln Asp Met Ala Val Glu Gly Ile Met Gly Ile Gln
                245                 250                 255

Val Asn Trp Asp Cys Asn Leu Asp Arg Ala Ala Ser Leu Cys Leu Pro
                260                 265                 270

Arg Tyr Ser Phe Arg Arg Leu Asp Thr Arg Asp Val Glu His Asn Val
                275                 280                 285

Ser Pro Gly Tyr Asn Phe Arg Phe Ala Lys Tyr Tyr Arg Asp Leu Ala
            290                 295                 300

Gly Asn Glu Gln Arg Thr Leu Ile Lys Ala Tyr Gly Ile Arg Phe Asp
305                 310                 315                 320

Ile Ile Val Phe Gly Lys Ala Gly Lys Phe Asp Ile Ile Pro Thr Met
                325                 330                 335

Ile Asn Ile Gly Ser Gly Leu Ala Leu Leu Gly Met Ala Thr Val Leu
            340                 345                 350

Cys Asp Ile Ile Val Leu Tyr Cys Met Lys Lys Arg Leu Tyr Tyr Arg
            355                 360                 365

Glu Lys Lys Tyr Lys Tyr Val Glu Asp Tyr Gln Gly Leu Ala Ser
370                 375                 380

Glu Leu Asp Gln
385

<210> SEQ ID NO 13
<211> LENGTH: 422
<212> TYPE: PRT
<213> ORGANISM: Homo sapiens

<400> SEQUENCE: 13

Met Gly Gln Ala Gly Cys Lys Gly Leu Cys Leu Ser Leu Phe Asp Tyr
1               5                   10                  15

Lys Thr Glu Lys Tyr Val Ile Ala Lys Asn Lys Lys Val Gly Leu Leu
            20                  25                  30

Tyr Arg Leu Leu Gln Ala Ser Ile Leu Ala Tyr Leu Val Val Trp Val
        35                  40                  45

Phe Leu Ile Lys Lys Gly Tyr Gln Asp Val Asp Thr Ser Leu Gln Ser
    50                  55                  60

Ala Val Ile Thr Lys Val Lys Gly Val Ala Phe Thr Asn Thr Ser Asp
65                  70                  75                  80

Leu Gly Gln Arg Ile Trp Asp Val Ala Asp Tyr Val Ile Pro Ala Gln
                85                  90                  95

Gly Glu Asn Val Phe Phe Val Val Thr Asn Leu Ile Val Thr Pro Asn
            100                 105                 110

Gln Arg Gln Asn Val Cys Ala Glu Asn Glu Gly Ile Pro Asp Gly Ala
        115                 120                 125
```

```
Cys Ser Lys Asp Ser Asp Cys His Ala Gly Glu Ala Val Thr Ala Gly
        130                 135                 140

Asn Gly Val Lys Thr Gly Arg Cys Leu Arg Arg Gly Asn Leu Ala Arg
145                 150                 155                 160

Gly Thr Cys Glu Ile Phe Ala Trp Cys Pro Leu Glu Thr Ser Ser Arg
                165                 170                 175

Pro Glu Glu Pro Phe Leu Lys Glu Ala Glu Asp Phe Thr Ile Phe Ile
            180                 185                 190

Lys Asn His Ile Arg Phe Pro Lys Phe Asn Phe Ser Lys Asn Asn Val
        195                 200                 205

Met Asp Val Lys Asp Arg Ser Phe Leu Lys Ser Cys His Phe Gly Pro
    210                 215                 220

Lys Asn His Tyr Cys Pro Ile Phe Arg Leu Gly Ser Ile Val Arg Trp
225                 230                 235                 240

Ala Gly Ser Asp Phe Gln Asp Ile Ala Leu Arg Gly Gly Val Ile Gly
                245                 250                 255

Ile Asn Ile Glu Trp Asn Cys Asp Leu Asp Lys Ala Ala Ser Glu Cys
            260                 265                 270

His Pro His Tyr Ser Phe Ser Arg Leu Asp Asn Lys Leu Ser Lys Ser
        275                 280                 285

Val Ser Ser Gly Tyr Asn Phe Arg Phe Ala Arg Tyr Tyr Arg Asp Ala
    290                 295                 300

Ala Gly Val Glu Phe Arg Thr Leu Met Lys Ala Tyr Gly Ile Arg Phe
305                 310                 315                 320

Asp Val Met Val Asn Gly Lys Gly Ala Phe Phe Cys Asp Leu Val Leu
                325                 330                 335

Ile Tyr Leu Ile Lys Lys Arg Glu Phe Tyr Arg Asp Lys Lys Tyr Glu
            340                 345                 350

Glu Val Arg Gly Leu Glu Asp Ser Gln Glu Ala Glu Asp Glu Ala
        355                 360                 365

Ser Gly Leu Gly Leu Ser Glu Gln Leu Thr Ser Gly Pro Gly Leu Leu
    370                 375                 380

Gly Met Pro Glu Gln Gln Glu Leu Gln Glu Pro Glu Ala Lys Arg
385                 390                 395                 400

Gly Ser Ser Ser Gln Lys Gly Asn Gly Ser Val Cys Pro Gln Leu Leu
                405                 410                 415

Glu Pro His Arg Ser Thr
            420

<210> SEQ ID NO 14
<211> LENGTH: 431
<212> TYPE: PRT
<213> ORGANISM: Homo sapiens

<400> SEQUENCE: 14

Met Gly Ser Pro Gly Ala Thr Thr Gly Trp Gly Leu Leu Asp Tyr Lys
1               5                   10                  15

Thr Glu Lys Tyr Val Met Thr Arg Asn Trp Arg Val Gly Ala Leu Gln
            20                  25                  30

Arg Leu Leu Gln Phe Gly Ile Val Val Tyr Val Val Gly Trp Ala Leu
        35                  40                  45

Leu Ala Lys Lys Gly Tyr Gln Glu Arg Asp Leu Glu Pro Gln Phe Ser
    50                  55                  60

Ile Ile Thr Lys Leu Lys Gly Val Ser Val Thr Gln Ile Lys Glu Leu
65                  70                  75                  80
```

Gly Asn Arg Leu Trp Asp Val Ala Asp Phe Val Lys Pro Pro Gln Gly
                    85                  90                  95

Glu Asn Val Phe Phe Leu Val Thr Asn Phe Leu Val Thr Pro Ala Gln
            100                 105                 110

Val Gln Gly Arg Cys Pro Glu His Pro Ser Val Pro Leu Ala Asn Cys
        115                 120                 125

Trp Val Asp Glu Asp Cys Pro Glu Gly Glu Gly Thr His Ser His
130                 135                 140

Gly Val Lys Thr Gly Gln Cys Val Val Phe Asn Gly Thr His Arg Thr
145                 150                 155                 160

Cys Glu Ile Trp Ser Trp Cys Pro Val Glu Ser Gly Val Val Pro Ser
                165                 170                 175

Arg Pro Leu Leu Ala Gln Ala Gln Asn Phe Thr Leu Phe Ile Lys Asn
            180                 185                 190

Thr Val Thr Phe Ser Lys Phe Asn Phe Ser Lys Ser Asn Ala Leu Glu
        195                 200                 205

Thr Trp Asp Pro Thr Tyr Phe Lys His Cys Arg Tyr Glu Pro Gln Phe
    210                 215                 220

Ser Pro Tyr Cys Pro Val Phe Arg Ile Gly Asp Leu Val Ala Lys Ala
225                 230                 235                 240

Gly Gly Thr Phe Glu Asp Leu Ala Leu Leu Gly Gly Ser Val Gly Ile
                245                 250                 255

Arg Val His Trp Asp Cys Asp Leu Asp Thr Gly Asp Ser Gly Cys Trp
            260                 265                 270

Pro His Tyr Ser Phe Gln Leu Gln Glu Lys Ser Tyr Asn Phe Arg Thr
        275                 280                 285

Ala Thr His Trp Trp Glu Gln Pro Gly Val Glu Ala Arg Thr Leu Leu
    290                 295                 300

Lys Leu Tyr Gly Ile Arg Phe Asp Ile Leu Val Thr Gly Gln Ala Gly
305                 310                 315                 320

Lys Phe Gly Leu Ile Pro Thr Ala Val Thr Leu Gly Thr Gly Ala Ala
                325                 330                 335

Trp Leu Gly Val Val Thr Phe Phe Cys Asp Leu Leu Leu Leu Tyr Val
            340                 345                 350

Asp Arg Glu Ala His Phe Tyr Trp Arg Thr Lys Tyr Glu Glu Ala Lys
        355                 360                 365

Ala Pro Lys Ala Thr Ala Asn Ser Val Trp Arg Glu Leu Ala Leu Ala
    370                 375                 380

Ser Gln Ala Arg Leu Ala Glu Cys Leu Arg Arg Ser Ser Ala Pro Ala
385                 390                 395                 400

Pro Thr Ala Thr Ala Ala Gly Ser Gln Thr Gln Thr Pro Gly Trp Pro
                405                 410                 415

Cys Pro Ser Ser Asp Thr His Leu Pro Thr His Ser Gly Ser Leu
            420                 425                 430

<210> SEQ ID NO 15
<211> LENGTH: 505
<212> TYPE: PRT
<213> ORGANISM: Homo sapiens

<400> SEQUENCE: 15

Met Thr Pro Gly Asp His Ser Trp Gly Asn Ser Phe Phe Val Met Thr
1               5                   10                  15

Asn Phe Leu Lys Thr Glu Gly Gln Glu Gln Arg Leu Cys Pro Glu Tyr
            20                  25                  30

```
Pro Thr Arg Arg Thr Leu Cys Ser Ser Asp Arg Gly Cys Lys Lys Gly
            35                  40                  45

Trp Met Asp Pro Gln Ser Lys Gly Ile Gln Thr Gly Arg Cys Val Val
 50                  55                  60

His Glu Gly Asn Gln Lys Thr Cys Glu Val Ser Ala Trp Cys Pro Ile
 65                  70                  75                  80

Glu Ala Val Glu Glu Ala Pro Arg Pro Ala Leu Leu Asn Ser Ala Glu
                    85                  90                  95

Asn Phe Thr Val Leu Ile Lys Asn Asn Ile Asp Phe Pro Gly His Asn
                100                 105                 110

Tyr Thr Thr Arg Asn Ile Leu Pro Gly Leu Asn Ile Thr Cys Thr Phe
                115                 120                 125

His Lys Thr Gln Asn Pro Gln Cys Pro Ile Phe Arg Leu Gly Asp Ile
            130                 135                 140

Phe Arg Glu Thr Gly Asp Asn Phe Ser Asp Val Ala Ile Gln Gly Gly
145                 150                 155                 160

Ile Met Gly Ile Glu Ile Tyr Trp Asp Cys Asn Leu Asp Arg Trp Phe
                165                 170                 175

His His Cys Arg Pro Lys Tyr Ser Phe Arg Arg Leu Asp Asp Lys Thr
            180                 185                 190

Thr Asn Val Ser Leu Tyr Pro Gly Tyr Asn Phe Arg Tyr Ala Lys Tyr
            195                 200                 205

Tyr Lys Glu Asn Asn Val Glu Lys Arg Thr Leu Ile Lys Val Phe Gly
210                 215                 220

Ile Arg Phe Asp Ile Leu Val Phe Gly Thr Gly Gly Lys Phe Asp Ile
225                 230                 235                 240

Ile Gln Leu Val Val Tyr Ile Gly Ser Thr Leu Ser Tyr Phe Gly Leu
                245                 250                 255

Ala Ala Val Phe Ile Asp Phe Leu Ile Asp Thr Tyr Ser Ser Asn Cys
                260                 265                 270

Cys Arg Ser His Ile Tyr Pro Trp Cys Lys Cys Cys Gln Pro Cys Val
            275                 280                 285

Val Asn Glu Tyr Tyr Arg Lys Lys Cys Glu Ser Ile Val Glu Pro
            290                 295                 300

Lys Pro Thr Leu Lys Tyr Val Ser Phe Val Asp Glu Ser His Ile Arg
305                 310                 315                 320

Met Val Asn Gln Gln Leu Leu Gly Arg Ser Leu Gln Asp Val Lys Gly
                325                 330                 335

Gln Glu Val Pro Arg Pro Ala Met Asp Phe Thr Asp Leu Ser Arg Leu
                340                 345                 350

Pro Leu Ala Leu His Asp Thr Pro Pro Ile Pro Gly Gln Pro Glu Glu
            355                 360                 365

Ile Gln Leu Leu Arg Lys Glu Ala Thr Pro Arg Ser Arg Asp Ser Pro
370                 375                 380

Val Trp Cys Gln Cys Gly Ser Cys Leu Pro Ser Gln Leu Pro Glu Ser
385                 390                 395                 400

His Arg Cys Leu Glu Glu Leu Cys Cys Arg Lys Lys Pro Gly Ala Cys
                405                 410                 415

Ile Thr Thr Ser Glu Leu Phe Arg Lys Leu Val Leu Ser Arg His Val
            420                 425                 430

Leu Gln Phe Leu Leu Leu Tyr Gln Glu Pro Leu Leu Ala Leu Asp Val
            435                 440                 445

Asp Ser Thr Asn Ser Arg Leu Arg His Cys Ala Tyr Arg Cys Tyr Ala
```

```
                    450                 455                 460
Thr Trp Arg Phe Gly Ser Gln Asp Met Ala Asp Phe Ala Ile Leu Pro
465                 470                 475                 480

Ser Cys Cys Arg Trp Arg Ile Arg Lys Glu Phe Pro Lys Ser Glu Gly
                    485                 490                 495

Gln Tyr Ser Gly Phe Lys Ser Pro Tyr
                    500                 505

<210> SEQ ID NO 16
<211> LENGTH: 425
<212> TYPE: PRT
<213> ORGANISM: Homo sapiens

<400> SEQUENCE: 16

Met Asp Gly Pro Ala Glu Gln Arg Pro Ala Leu Leu Asn Ser Ala Glu
1               5                   10                  15

Asn Phe Thr Val Leu Ile Lys Asn Asn Ile Asp Phe Pro Gly His Asn
            20                  25                  30

Tyr Thr Thr Arg Asn Ile Leu Pro Gly Leu Asn Ile Thr Cys Thr Phe
        35                  40                  45

His Lys Thr Gln Asn Pro Gln Cys Pro Ile Phe Arg Leu Gly Asp Ile
    50                  55                  60

Phe Arg Glu Thr Gly Asp Asn Phe Ser Asp Val Ala Ile Gln Gly Gly
65                  70                  75                  80

Ile Met Gly Ile Glu Ile Tyr Trp Asp Cys Asn Leu Asp Arg Trp Phe
                85                  90                  95

His His Cys Arg Pro Lys Tyr Ser Phe Arg Arg Leu Asp Asp Lys Thr
            100                 105                 110

Thr Asn Val Ser Leu Tyr Pro Gly Tyr Asn Phe Arg Tyr Ala Lys Tyr
        115                 120                 125

Tyr Lys Glu Asn Asn Val Glu Lys Arg Thr Leu Ile Lys Val Phe Gly
    130                 135                 140

Ile Arg Phe Asp Ile Leu Val Phe Gly Thr Gly Gly Lys Phe Asp Ile
145                 150                 155                 160

Ile Gln Leu Val Val Tyr Ile Gly Ser Thr Leu Ser Tyr Phe Gly Leu
                165                 170                 175

Ala Ala Val Phe Ile Asp Phe Leu Ile Asp Thr Tyr Ser Ser Asn Cys
            180                 185                 190

Cys Arg Ser His Ile Tyr Pro Trp Cys Lys Cys Gln Pro Cys Val
        195                 200                 205

Val Asn Glu Tyr Tyr Arg Lys Cys Glu Ser Ile Val Glu Pro
210                 215                 220

Lys Pro Thr Leu Lys Tyr Val Ser Phe Val Asp Glu Ser His Ile Arg
225                 230                 235                 240

Met Val Asn Gln Gln Leu Leu Gly Arg Ser Leu Gln Asp Val Lys Gly
                245                 250                 255

Gln Glu Val Pro Arg Pro Ala Met Asp Phe Thr Asp Leu Ser Arg Leu
            260                 265                 270

Pro Leu Ala Leu His Asp Thr Pro Ile Pro Gly Gln Pro Glu Glu
        275                 280                 285

Ile Gln Leu Leu Arg Lys Glu Ala Thr Pro Arg Ser Arg Asp Ser Pro
    290                 295                 300

Val Trp Cys Gln Cys Gly Ser Cys Leu Pro Ser Gln Leu Pro Glu Ser
305                 310                 315                 320

His Arg Cys Leu Glu Glu Leu Cys Cys Arg Lys Lys Pro Gly Ala Cys
```

```
                  325                 330                 335
Ile Thr Thr Ser Glu Leu Phe Arg Lys Leu Val Leu Ser Arg His Val
                340                 345                 350

Leu Gln Phe Leu Leu Leu Tyr Gln Glu Pro Leu Leu Ala Leu Asp Val
                355                 360                 365

Asp Ser Thr Asn Ser Arg Leu Arg His Cys Ala Tyr Arg Cys Tyr Ala
                370                 375                 380

Thr Trp Arg Phe Gly Ser Gln Asp Met Ala Asp Phe Ala Ile Leu Pro
385                 390                 395                 400

Ser Cys Cys Arg Trp Arg Ile Arg Lys Glu Phe Pro Lys Ser Glu Gly
                405                 410                 415

Gln Tyr Ser Gly Phe Lys Ser Pro Tyr
                420                 425

<210> SEQ ID NO 17
<211> LENGTH: 354
<212> TYPE: PRT
<213> ORGANISM: Homo sapiens

<400> SEQUENCE: 17

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
                20                  25                  30

Phe His Val Ile Ile Phe Ser Tyr Val Cys Phe Ala Leu Val Ser Asp
                35                  40                  45

Lys Leu Tyr Gln Arg Lys Glu Pro Val Ile Ser Ser Val His Thr Lys
        50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
                100                 105                 110

Gly Gln Glu Gln Arg Leu Cys Pro Glu Tyr Pro Thr Arg Arg Thr Leu
            115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
                180                 185                 190

Lys Asn Asn Ile Asp Phe Pro Gly His Asn Tyr Thr Thr Arg Asn Ile
                195                 200                 205

Leu Pro Gly Leu Asn Ile Thr Cys Thr Phe His Lys Thr Gln Asn Pro
        210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
                260                 265                 270

Tyr Ser Phe Arg Arg Leu Asp Asp Lys Thr Thr Asn Val Ser Leu Tyr
```

```
            275                 280                 285
Pro Gly Tyr Asn Phe Arg Tyr Ala Lys Tyr Lys Glu Asn Asn Val
290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Val Arg Asp Ser Glu Gly
                340                 345                 350

Ser Asp

<210> SEQ ID NO 18
<211> LENGTH: 306
<212> TYPE: PRT
<213> ORGANISM: Homo sapiens

<400> SEQUENCE: 18

Met Trp Gln Phe Arg Tyr Ala Lys Tyr Lys Glu Asn Asn Val Glu
1               5                   10                  15

Lys Arg Thr Leu Ile Lys Val Phe Gly Ile Arg Phe Asp Ile Leu Val
                20                  25                  30

Phe Gly Thr Gly Gly Lys Phe Asp Ile Ile Gln Leu Val Val Tyr Ile
            35                  40                  45

Gly Ser Thr Leu Ser Tyr Phe Gly Leu Ala Ala Val Phe Ile Asp Phe
        50                  55                  60

Leu Ile Asp Thr Tyr Ser Ser Asn Cys Cys Arg Ser His Ile Tyr Pro
65                  70                  75                  80

Trp Cys Lys Cys Cys Gln Pro Cys Val Val Asn Glu Tyr Tyr Arg
                85                  90                  95

Lys Lys Cys Glu Ser Ile Val Glu Pro Lys Pro Thr Leu Lys Tyr Val
                100                 105                 110

Ser Phe Val Asp Glu Ser His Ile Arg Met Val Asn Gln Gln Leu Leu
            115                 120                 125

Gly Arg Ser Leu Gln Asp Val Lys Gly Gln Glu Val Pro Arg Pro Ala
        130                 135                 140

Met Asp Phe Thr Asp Leu Ser Arg Leu Pro Leu Ala Leu His Asp Thr
145                 150                 155                 160

Pro Pro Ile Pro Gly Gln Pro Glu Glu Ile Gln Leu Leu Arg Lys Glu
                165                 170                 175

Ala Thr Pro Arg Ser Arg Asp Ser Pro Val Trp Cys Gln Cys Gly Ser
            180                 185                 190

Cys Leu Pro Ser Gln Leu Pro Glu Ser His Arg Cys Leu Glu Glu Leu
        195                 200                 205

Cys Cys Arg Lys Lys Pro Gly Ala Cys Ile Thr Thr Ser Glu Leu Phe
    210                 215                 220

Arg Lys Leu Val Leu Ser Arg His Val Leu Gln Phe Leu Leu Leu Tyr
225                 230                 235                 240

Gln Glu Pro Leu Leu Ala Leu Asp Val Asp Ser Thr Asn Ser Arg Leu
                245                 250                 255

Arg His Cys Ala Tyr Arg Cys Tyr Ala Thr Trp Arg Phe Gly Ser Gln
            260                 265                 270

Asp Met Ala Asp Phe Ala Ile Leu Pro Ser Cys Cys Arg Trp Arg Ile
        275                 280                 285

Arg Lys Glu Phe Pro Lys Ser Glu Gly Gln Tyr Ser Gly Phe Lys Ser
    290                 295                 300
```

Pro Tyr
305

<210> SEQ ID NO 19
<211> LENGTH: 275
<212> TYPE: PRT
<213> ORGANISM: Homo sapiens

<400> SEQUENCE: 19

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Tyr Ala Lys
        195                 200                 205

Tyr Tyr Lys Glu Asn Asn Val Glu Lys Arg Thr Leu Ile Lys Val Phe
    210                 215                 220

Gly Ile Arg Phe Asp Ile Leu Val Phe Gly Thr Gly Gly Lys Phe Asp
225                 230                 235                 240

Ile Ile Gln Leu Val Val Tyr Ile Gly Ser Thr Leu Ser Tyr Phe Gly
                245                 250                 255

Leu Val Arg Asp Ser Leu Phe His Ala Leu Gly Lys Trp Phe Gly Glu
            260                 265                 270

Gly Ser Asp
        275

<210> SEQ ID NO 20
<211> LENGTH: 274
<212> TYPE: PRT
<213> ORGANISM: Homo sapiens

<400> SEQUENCE: 20

Met Thr Pro Gly Asp His Ser Trp Gly Asn Ser Phe Phe Val Met Thr
1               5                   10                  15

Asn Phe Leu Lys Thr Glu Gly Gln Glu Gln Arg Leu Cys Pro Glu Tyr
            20                  25                  30

```
Pro Thr Arg Arg Thr Leu Cys Ser Ser Asp Arg Gly Cys Lys Lys Gly
            35                  40                  45

Trp Met Asp Pro Gln Ser Lys Gly Ile Gln Thr Arg Cys Val Val
 50                  55                  60

His Glu Gly Asn Gln Lys Thr Cys Glu Val Ser Ala Trp Cys Pro Ile
 65                  70                  75                  80

Glu Ala Val Glu Glu Ala Pro Arg Pro Ala Leu Leu Asn Ser Ala Glu
                    85                  90                  95

Asn Phe Thr Val Leu Ile Lys Asn Asn Ile Asp Phe Pro Gly His Asn
                100                 105                 110

Tyr Thr Thr Arg Asn Ile Leu Pro Gly Leu Asn Ile Thr Cys Thr Phe
            115                 120                 125

His Lys Thr Gln Asn Pro Gln Cys Pro Ile Phe Arg Leu Gly Asp Ile
130                 135                 140

Phe Arg Glu Thr Gly Asp Asn Phe Ser Asp Val Ala Ile Gln Gly Gly
145                 150                 155                 160

Ile Met Gly Ile Glu Ile Tyr Trp Asp Cys Asn Leu Asp Arg Trp Phe
                165                 170                 175

His His Cys Arg Pro Lys Tyr Ser Phe Arg Arg Leu Asp Asp Lys Thr
                180                 185                 190

Thr Asn Val Ser Leu Tyr Pro Gly Tyr Asn Phe Arg Tyr Ala Lys Tyr
            195                 200                 205

Tyr Lys Glu Asn Asn Val Glu Lys Arg Thr Leu Ile Lys Val Phe Gly
210                 215                 220

Ile Arg Phe Asp Ile Leu Val Phe Gly Thr Gly Gly Lys Phe Asp Ile
225                 230                 235                 240

Ile Gln Leu Val Val Tyr Ile Gly Ser Thr Leu Ser Tyr Phe Gly Leu
                245                 250                 255

Val Arg Asp Ser Leu Phe His Ala Leu Gly Lys Trp Phe Gly Glu Gly
                260                 265                 270

Ser Asp

<210> SEQ ID NO 21
<211> LENGTH: 258
<212> TYPE: PRT
<213> ORGANISM: Homo sapiens

<400> SEQUENCE: 21

Met Pro Ala Cys Cys Ser Cys Ser Asp Val Phe Gln Tyr Glu Thr Asn
 1               5                  10                  15

Lys Val Thr Arg Ile Gln Ser Met Asn Tyr Gly Thr Ile Lys Trp Phe
                20                  25                  30

Phe His Val Ile Ile Phe Ser Tyr Val Cys Phe Ala Leu Val Ser Asp
            35                  40                  45

Lys Leu Tyr Gln Arg Lys Glu Pro Val Ile Ser Ser Val His Thr Lys
 50                  55                  60

Val Lys Gly Ile Ala Glu Val Lys Glu Glu Ile Val Glu Asn Gly Val
 65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
                100                 105                 110

Gly Gln Glu Gln Arg Leu Cys Pro Glu Tyr Pro Thr Arg Arg Thr Leu
            115                 120                 125

Cys Ser Ser Asp Arg Gly Cys Lys Lys Gly Trp Met Asp Pro Gln Ser
```

```
                130                 135                 140
Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
                180                 185                 190

Lys Asn Asn Ile Asp Phe Pro Gly His Asn Tyr Thr Thr Arg Asn Ile
                195                 200                 205

Leu Pro Gly Leu Asn Ile Thr Cys Thr Phe His Lys Thr Gln Asn Pro
            210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Ile Arg Gln Val Leu Gln Gly Lys
                245                 250                 255

Gln Cys

<210> SEQ ID NO 22
<211> LENGTH: 128
<212> TYPE: PRT
<213> ORGANISM: Homo sapiens

<400> SEQUENCE: 22

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
                20                  25                  30

Phe His Val Ile Ile Phe Ser Tyr Val Cys Phe Ala Leu Val Ser Asp
                35                  40                  45

Lys Leu Tyr Gln Arg Lys Glu Pro Val Ile Ser Ser Val His Thr Lys
            50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
                100                 105                 110

Gly Gln Glu Gln Arg Leu Cys Pro Glu Glu Phe Arg Pro Glu Gly Val
            115                 120                 125
```